United States Patent [19]
Goldrick

[11] Patent Number: 5,891,629
[45] Date of Patent: Apr. 6, 1999

[54] COMPOSITIONS FOR IMPROVING RNASE CLEAVAGE OF BASE PAIR MISMATCHES IN DOUBLE-STRANDED NUCLEIC ACIDS

[75] Inventor: Marianna M. Goldrick, Pflugerville, Tex.

[73] Assignee: Ambion, Inc., Austin, Tex.

[21] Appl. No.: 534,977

[22] Filed: Sep. 28, 1995

[51] Int. Cl.$^6$ .............................. C12Q 1/68; C12P 19/34
[52] U.S. Cl. .............................................. 435/6; 435/91.2
[58] Field of Search ................................. 435/5, 6, 91.2; 935/77, 78

[56] References Cited

U.S. PATENT DOCUMENTS

| | | | |
|---|---|---|---|
| 4,683,202 | 7/1987 | Mullis | 435/91 |
| 4,946,773 | 8/1990 | Maniatis et al. | 435/6 |
| 5,476,774 | 12/1995 | Wang et al. | 435/91.2 |
| 5,571,905 | 11/1996 | Vogelstein et al. | 536/24.31 |
| 5,576,422 | 11/1996 | Vogelstein et al. | 530/350 |
| 5,582,986 | 12/1996 | Monia et al. | 435/6 |
| 5,589,329 | 12/1996 | Winkler et al. | 435/5 |
| 5,599,673 | 2/1997 | Keating et al. | 435/6 |
| 5,602,243 | 2/1997 | Vogelstein | 536/24.3 |

FOREIGN PATENT DOCUMENTS

| | | |
|---|---|---|
| 0 329 311 | 8/1989 | European Pat. Off. . |
| 2 179 735 | 3/1987 | United Kingdom . |
| WO 91/15600 | 10/1991 | WIPO . |
| WO 93/20233 | 10/1993 | WIPO . |

OTHER PUBLICATIONS

Cristina et al., "Analysis of Genetic Variability in Human Respiratory Syncytial Virus by the RNase A Mismatch Cleavage Method: Subtype Divergence and Heterogeneity," *Virology*, 174:126–134, 1990.

Christina et al., "Evolution of the G and P Genes of Human Respiratory Syncytial Virus (Subgroup A) Studied by the RNase A Mismatch Cleaveage Method," *Virology*, 184:210–218, 1991.

Dunn et al., "Identification of Germline and Somatic Mutations Affecting the Retinoblastoma Gene", *Science*, 241:1797–1800, 1988.

Friedberg et al., "Selective Detection of mRNA Forms Encoding the Major Phenobarbital Inducible Cytochromes P450 and Other Members of the P45011B Family by the RNAse A Protection Assay", *Archives of Biochemistry and Biophysics*, 279:(1)167–173, 1990.

Genovese et al., "Detection of Mutations In Human Type I Collagen mRNA in Osteogenesis Imperfecta by Indirect RNase Protection", *J. Biol. Chem.*, 264:(16)9632–9637, 1989.

Gibbs and Caskey, "Identification and Localization of Mutations at the Lesch–Nyhan Locus by Ribonuclease A Cleavage," *Science*, 236:303–305, 1987.

Gilman, "Ribonuclease Protection Assay", *Current Protocols in Molecular Biology*, Ausubel, F.N. et al., Ed., Unit 4.7:4.7.1–4.7.8, 1987, Mass. Gen. Hosp., Harvard Med. School, Boston, MA.

Goldrick, M., "Faster Mutation Analysis. Non–Isotopic Method Offers Advantages Over SSCP," Ambion Tech-Notes, 2(1):1–13, Ambion, Inc., Austin, Texas, 1995.

Kain et al., "Universal Promoter for Gene Expression Without Cloning: Expression–PCR", *BioTechniques*, 10:(3)366–373, 1991.

Kim et al., "Occurrence of p53 Gene Abnormalities in Gastric Carcinoma Tumors and Cell Lines", *J. Natl. Cancer Res.*, 83:(13)938–943, 1991.

Kinzler et al., "Identification of a Gene Located at Chromosome 5q21 That is Mutated in Colorectal Cancers", *Science*, 251:1366–1370, 1991.

Krause et al., "[44] Solution Hybridization–Nuclease Protection Assays for Sensitive Detection of Differentially Spliced Substance P–and Neurokinin A–Encoding Messenger Ribonucleic Acids", *Methods in Enzymology*, 168:634–653.

Lopez–Galindez et al., "Characterization of genetic variation and 3'–azido–3' seoxythymidine–resistance mutations of human immunodeficiency virus by the RNase A mismatch cleavage method," *Proc. Natl. Acad. Sci USA*, 88:4280–4284, 1991.

Marquardt, et al., "Detection and localization of single–base sequence differences in foot–and–mouth disease virus genomes by the RNase mismatch cleavage method," *Journal of Virological Methods*, 33:267–282, May 1991.

Melton et al., "Efficient in vitro Synthesis of Biologically Active RNA and RNA Hybridization Probes for Plasmids Containing a Bacteriophage SP6 Promoter," *Nucleic Acids Res.*, 12:7035–7056, 1984.

Myers et al., "Detection of Single Base Substitutions by Ribonuclease Cleavage at Mismatches in RNA:DNA Duplexes", *Science*, 230:1242–1246, 1985.

Myers et al., "Recent Advances in the Development of Methods for Detecting Single–base Substitutions Associated with Human Genetic Diseases", *Cold Spring Harbor Symposia On Quantitative Biology*, LI:275–284.

Nishisho et al., "Mutations of Chromosome 5q21 Genes in FAP and Colorectal Cancer Patients" *Science*, 253:665–669, 1991.

Perucho, "Detection of Single–base Substitutions with the RNAse A Mismatch Cleavage Method", *Strategies in Molecular Biol.*, 2:(3)37–41, 1989.

(List continued on next page.)

*Primary Examiner*—Eggerton A. Campbell
*Attorney, Agent, or Firm*—Arnold, White & Durkee

[57] ABSTRACT

The present invention addresses compositions and methods for cleaving nucleic acids. The invention allows one to reliably detecting point mutations in long and short target regions of nucleic acids in a safe, non-labor intensive, and cost effective manner. The methods and compositions of the present invention allow for the use of various RNases, such as RNase A, RNase I and RNase T2, in the detection of mutations. The present invention also identifies reaction conditions that result in significant improvement in specific mismatch cleavage in the NIRCA™ assay.

51 Claims, 8 Drawing Sheets

OTHER PUBLICATIONS

Raines, R.T., "Structure, Mechanism and Function of Ribonucleases," Proceedings of the Second International Meeting, pp. 139–143, Universitat Autonoma de Barcelona, Bellaterra, Spain, 1991 (Cuchillo et al., eds.).

Resto et al., "Amplification of Protein Expression in a Cell Free System", *Nucleic Acids Research*, 20:(22)5979–5983, 1992.

Rosenzweig, "Preclinical Diagnosis of Familial Hypertrophic Cardiomyopathy by Genetic Analysis of Blood Lymphocytes", *New Engl. J. Med.*, 325:(25)1753–1760, 1991.

Sambrook et al., "Molecular Cloning; Mapping Of RNA With Ribonuclease And Radiolabeled RNA Probes", *Cold Spring Harbor Laboratory Press*, 7.71–7.77, 1989.

Sarkar et al., "Access to a Messenger RNA Sequence or Its Protein Product Is Not Limited by Tissue or Species Specificity", *Science*, 244:331–334, 1989.

Stoflet et al., "Genomic Amplification with Transcript Sequencing", *Science*, 239:491–494, 1988.

Storch et al., "RNA Fingerprinting of Respiratory Syncytial Virus Using Ribonuclease Protection", *J. Clin. Invest.*, 83:1894–1902, 1989.

Takahashi et al., "p53: A Frequent Target for Genetic Abnormalities in Lung Cancer", *Science*, 246:491–494, 1989.

Theophilus et al., "Comparison of RNase A, a chemical cleavage and GC–clamped denaturing gradient gel electrophoresis for the detection of mutations in exon 9 of the human acid b–glucosidase gene," *Nucleic Acids Res.*, 17(19):7707–7722, 1989.

Ueda et al., "Detection of Multidrug Resistance (MDR1) Gene RNA Expression in Human Tumors by a Sensitive Ribonuclease Protection Assay", *Jpn. J. Cancer Res.*, 80:1127–1132, 1989.

Watkins et al., "Characteristics and Prognostic Implications Of Myosin Missense Mutations In Familial Hypertrophic Cardiomyopathy", *New Engl. J. Med.* 326:(17)1108–1114, 1992.

Winter et al., "A Method to Detect and Characterize Point Mutations in Transcribed Genes: Amplification and Overexpression of the Mutant c–Ki–ras Allele in Human Tumor Cells", *Proc. Natl. Acad. Sci. USA*, 82:7575–7579, 1985.

Yang and Melera, "Application of the Polymerase Chain Reaction to the Ribonuclease Protection Assay," *BioTechniques*, 13(6)922–927, 1992.

International Search Report dated Jun. 27, 1996.

U.S. application No. 08/371,531, filed Jan. 9, 1995, Inventor Marianna Goldrick.

Almoguera et al., "Application of the Polymerase Chain Reaction for the Detection of Single–Base Substitutions by the RNase–A Mismatch Cleavage Method," pp. 37–45.

COMPOSITIONS FOR IMPROVING RNASE CLEAVAGE OF BASE PAIR MISMATCHES IN DOUBLE-STRANDED NUCLEIC ACIDS

The government may own rights in the present invention pursuant to U.S. grant number CA57045.

BACKGROUND OF THE INVENTION

1. Field of the invention

The invention relates to improved compositions and methods for the digestion of nucleic acids, specifically, to improved compositions and methods for cleaving base pair mismatches in double-stranded nucleic acid targets. More particularly, the invention concerns novel components of the reaction mixture in which RNase is used to cleave nucleic acids, and in particular base pair mismatches.

2. Description of the Art

The digestion of nucleic acids has important applications in the field of molecular biology. For example, digestion of single base mismatches in RNA/DNA and RNA/RNA targets has been used to detect mutations.

Nucleases are enzymes used to digest nucleic acid. DNases degrade single and/or double-stranded DNA, RNases degrade single and/or double-stranded RNA, and non-specific nucleases such as SI degrade both RNA and DNA, with preference for single-stranded nucleic acid. Nucleases are enzymes that catalyze the hydrolytic cleavage of a polynucleotide chain by cleaving the phosphodiester linkage between nucleotide residues. They can be classified as either exonucleases, which cleave nucleotides from the end of the chain, or endonucleases, which cleave from within the chain, and may specifically cleave single stranded or double stranded nucleic acids or both. Nucleases may also act only or preferentially on DNA, DNases, or RNA, RNases, or they may cleave both. Most nucleases cleave the nucleic acids without sequence specificity. However, some nucleases cleave specifically in a particular base or a specific sequence, such as restriction enzymes.

The use of nucleases to digest or cleave nucleic acids is well known in the field of molecular biology. For example, nucleases can be used to digest base pair mismatches that result from point mutations in genes. In the case of detecting mutations by digestion or cleavage the only nucleases which have been widely used are single-strand specific RNases; in particular, RNase A has been used for this purpose.

Methods for rapidly, reliably, and inexpensively detecting new point mutations have wide application in diagnosis and treatment of genetic diseases and cancer, and also in genetic counseling. These methods are of great benefit as well in basic research into the causes of a variety of human genetic diseases and in establishing human genetic linkage maps.

In most genetic diseases, the causative mutations are widely distributed over a large number of sites. Relatively few genetic disorders are caused by defined mutations at single sites; sickle cell anemia is one example of a disease phenotype that is always caused by the same specific mutation (i.e., an A–>T transversion at codon 6 of the beta-globin gene). More commonly, genetic diseases, especially cancer, are associated with a number of different mutations in different sites in different arrays of genes. An example of this is breast cancer. For instance, mutations in the recently identified BRCA1 gene, which is thought to be associated with familial breast cancer, are scattered throughout a 5 kilobase coding region. Dispersed mutations in several other genes, including p53, EGFR, IGR, and her2/neu, are also believed to play important roles in breast cancer.

Methods for genetic screening by identifying mutations associated with most genetic diseases and cancer must be able to assess large regions of the genome. Once a relevant mutation has been identified in a given patient, other family members and affected individuals can be screened using methods which are targeted to that site. The ability to detect dispersed point mutations is critical for genetic counseling, diagnosis, and early clinical intervention as well as for research into the etiology of cancer and other genetic disorders. The ideal method for genetic screening would quickly, inexpensively, and accurately detect all types of widely dispersed mutations in genomic DNA, cDNA, and RNA samples, depending on the specific situation. Currently there are no methods which achieve these goals.

Historically, a number of different methods have been used to detect point mutations, including denaturing gradient gel electrophoresis ("DGGE"), restriction enzyme polymorphism analysis, chemical and enzymatic cleavage methods, and others (Cotton, 1989). The more common procedures currently in use include direct sequencing of target regions amplified by PCR and single-strand conformation polymorphism analysis ("SSCP").

Direct sequencing of PCR products is considered to be the most reliable method for identifying new mutations. However, sequencing is also the most expensive and labor-intensive genetic screening method. Direct sequencing is typically the most time-consuming step in the identification of point mutations, even with the advent of automated sequencing methods. Further, even DNA sequencing may not give a clear indication of a point mutation in some cases, for example when an individual is heterozygous for that allele. Non-specific background signals are often present in sequencing reactions, appearing as coincident bands on the sequencing ladder in manual sequencing methods using radioisotopes (Cheng and Haas, 1992), or appearing as non-specific fluorescent peaks in automated sequencing reactions. The main causes of this type of background are premature termination during the extension reaction and non-specific priming. Due to these limitations, and to the time and expense involved in sequencing large regions of DNA, direct sequencing is more practical as a tool to identify the specific nucleotide alterations in samples known to contain mutations, rather than as a primary screening method to assess large regions of the genome. Therefore, preliminary screening methods are needed to identify samples that contain mutations, and avoid the unnecessary labor, expense, and time needed for sequencing samples which do not contain mutations.

The most common screening method currently in use is SSCP. This method involves amplification of target regions, usually less than 300 bp long, which are denatured and separated on thin, native polyacrylamide gels. Point mutations are detected as mobility differences between wild-type controls and experimental samples. One drawback of SSCP is the requirement for radiolabeled material for analysis, due to the small mass amounts of the double-stranded DNA samples that must be used to prevent reannealing of the complementary strands after denaturation. Another disadvantage of SSCP is that the gels typically require long running periods (6–18 hours or longer) at high voltages, usually in a cold room with recirculation of the running buffer. These electrophoresis parameters are awkward, labor-intensive, hazardous, and require the use of expensive and specialized equipment. In addition, no single, optimal electrophoresis condition or gel composition for detection of mutations by SSCP, has yet been discovered. Therefore, each sample is typically assessed on multiple gels (for example, with and without 10% glycerol, or at room temperature and 4° C.). Further, as the size of the target region assessed by SSCP increases, the detection rate decreases. For example, in one study, the detection rate decreased to 57% in 307 bp targets (Sarker et al., 1992). Therefore, SSCP is not effective for screening large regions of the genome in a single step.

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations. U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase can be inactivated by proteolytic digestion and organic extraction, and the cleavage products are denatured by heating and analyzed by electrophoresis on denaturing polyacrylamide gels. For the analysis of cleavage products, the single-stranded products of the RNase A treatment are electrophoretically separated according to size and compared to similarly treated control duplexes. Currently available RNase mismatch cleavage assays, including those performed according to U.S. Pat. No. 4,946,773, require the use of radiolabeled RNA probes. The use of radiolabeled probes has many drawbacks, including the expense of the isotope, the time delay required for film exposure, and, particularly, the hazard radioisotopes present to workers during their synthesis, purification, and use at close range in the assay. The problems and costs associated with disposal of radioactive waste are also serious and well-documented. Further drawbacks of RNase mismatch cleavage assays in their present form, include the fact that only about one half to two thirds of point mutations are detected (Myers et al., 1985; Theophillus et al., 1989; Grompe, 1993). In light of these limitations, RNase mismatch cleavage assays have largely fallen into disuse.

The inventor has recently filed a U.S. patent application (Application No. 08/371,531, incorporated herein by reference) disclosing an RNase protection assay in which RNA transcripts of test sample and controls are produced by in vitro transcription of PCR products containing opposable T7 and SP6 phage promoter sequences. No radioisotopes are required in the disclosed method, termed non-isotopic RNase cleavage assay ("NIRCA™"), since the dual amplification steps of PCR and in vitro transcription yield large amounts (several micrograms) of target substrate, which permits the cleavage products to be visualized directly under UV light, when stained with ethidium bromide.

Sensitivity (i.e., the ability to detect 100% of all mutations) and specificity (lack of false positives) are important requirements for widespread acceptance of any new method for genetic screening. Even though the NIRCA™ method is a considerable improvement over past systems, there is still a drawback in that not all point mutations are detected by NIRCA™. For example, while 90% of 30 point mutations were detected in an X-linked gene in the initial controlled study reported in the 08/371,531 application (along with two false positives in the 19 normal controls), the detection rate in a heterozygous system is likely to be less. In a clinical/diagnostic setting, where the majority of samples are normal in any give locus, the occurrence of even a low percentage of false positives could result in higher than desirable error rates. Of greater concern in clinical settings is the occurrence of false negatives, since overlooked mutations may result in improper diagnosis, treatment, and counseling. The reduced sensitivity of NIRCA™, relative to more laborious and expensive screening methods (e.g., SSCP, DGGE, direct sequencing) is its major disadvantage. A method to improve the sensitivity of the NIRCA™ assay would increase its utility for mutation detection and genetic analysis in many areas of basic and applied research, as well as in clinical/diagnostic settings.

Myers and Maniatis in U.S. Pat. No. 4,946,773 describe the detection of base pair mismatches using RNase A. Non-specific cleavage seen with RNase A has been a significant problem (Theophillus et al., 1989; Maniatis et al., U.S. Pat. No. 4,946,773). RNase A levels needed for optimum cleavage of mismatches are so high as to cause significant non-specific cleavage in the no-mismatch controls. Non-specific cleavage by RNase I has also been reported to be a problem when using this enzyme for mismatch detection. In the only currently known example of a method that employs RNase I for mismatch cleavage, the amount of RNase I used to cleave mismatches results in partial degradation of the base paired duplex. (Promega Technical Manual, 1994). Non-specific cleavage of the double-stranded duplex makes interpretation of the data more difficult and error-prone. Indeed, the two false-positive samples the inventor misidentified in an initial controlled study may be attributed to the high background of non-specific cleavage products.

Subsequent to the issue of the Myers and Maniatis patent, the *E. coli* enzyme, RNase I, which had been characterized as having a broader substrate specificity, was tested by the inventor for use in mismatch assays. This suggests that RNase I is a desirable enzyme to employ in the detection of base pair mismatches if components can be found to decrease the extent of non-specific cleavage and increase the frequency of cleavage of mismatches.

Unfortunately, the use of RNase I has proven difficult. The use of RNase I for mismatch detection is described in literature from Promega Biotech (Ekenberg and Hudson, 1994). Promega markets a kit containing RNase I that is shown in their literature to cleave three out of four known mismatches, provided the enzyme level is sufficiently high. One drawback of the Promega kit is that a very large amount of the RNase I enzyme must be used. For detection of single base mismatches, the Promega Technical Manual recommends using approximately 100 times more RNase I than is normally used in the standard RNase detection assay.

For example, in a commercial product marketed by Ambion, Inc. (Austin, Tex.) for mutation detection using the NIRCA™ method, two different RNase compositions are provided to be tried and adopted at user discretion. One composition contains a combination of RNase A (approximately 0.5 $\mu$g/ml) and RNase I (approximately 175 units/ml), and the other contains RNase A only (approximately 14 $\mu$g/ml), where these amounts refer to the recommended final working concentrations.

Despite the favorable characteristics of RNase I, the fact that approximately 100 times as much RNase I as RNase A is needed for an assay procedure has effectively prevented the use of RNase I for detecting base pair mismatches. Of even greater concern is the fact that even when the recommended high levels of RNase I are used, many single-base mismatches are not cleaved using the reaction mixture in the Promega Technical Manual (FIG. 1).

Therefore, a need exists for a sensitive technique that reliably detects point mutations in long target regions of nucleic acids in a safe, easy, cost effective way. Particularly advantageous would be such a method that would lend itself to the use of various RNase enzymes and that would not require radioactively labeled components.

SUMMARY OF THE INVENTION

The present invention seeks to overcome drawbacks in previously disclosed methods for cleaving base pair mismatches in target nucleic acids with nucleases. The present invention improves on the present mismatch cleavage methods by providing a method that is faster and less labor intensive, that does not require the use of radioisotopes and, most importantly, that results in a significant improvement in mutation detection rate.

More specifically, the present invention represents a major technical advance by identifying reaction conditions which result in significant improvement in specific mismatch cleavage.

The present invention also seeks to overcome the drawbacks inherent in the NIRCA™ method and the other known mutation detection methods by improving the frequency and extent of cleavage of base pair mismatches in double stranded nucleic acid targets. The present invention provides a novel reaction mixture which increases the ability of RNases, particularly RNase I and RNase T1, to specifically cleave base pair mismatches in duplex nucleic acids. The invention concerns compositions for performing the RNase digestion step of the assay, which differ substantially from any which have been previously described. The invention reduces non-specific cleavage and the amount of enzyme needed for cleavage of mismatches for at least some RNases, and results in the cleavage of many base pair mismatches which are completely resistant to cleavage under previously reported conditions.

The invention also results in more complete cleavage of many mismatches which were only partially or marginally cleaved under known conditions. The reduction in non-specific cleavage and increase in frequency and extent of mismatch cleavage result in a significant improvement in the sensitivity and specificity of the RNase cleavage-based genetic screening assay. In addition, the invention appears to increase the activity of at least some RNases on single-stranded substrates, that is, the single-stranded substrates will be degraded at lower enzyme concentrations than would otherwise be required.

The present invention represents a major technical advance by identifying reaction conditions which result in significant improvement in specific mismatch cleavage in the NIRCA™ assay. The invention is also expected to improve detection of mutations using the methods of the conventional RNase cleavage assay (Myers et al., 1985; Maniatis et al., U.S. Pat. No. 4,946,773, 1990), where cleavage products are denatured and analyzed as single strands. This is because any agent which improves cleavage of both mismatched strands must necessarily improve cleavage of the individual strands.

A. REACTION MIXTURES FOR IMPROVED NUCLEIC ACID CLEAVAGE

A basic aspect of the present invention encompasses a reaction mixture comprising: an RNase enzyme; a nucleic acid intercalating agent; and an agent which enhances RNase mismatch cleavage activity, said agent comprising a digested protein mixture, a divalent cation, or both. As used herein the phrase "RNase mismatch cleavage activity enhancing agent" refers to a compound or mixture of compounds that increase the ability to detect mutations mismatches by increasing the specific cleavage of base pair mismatches.

1. The Digested Protein Mixture Component

A preferred embodiment of the invention is a reaction mixture wherein the RNase mismatch cleavage activity enhancing agent comprises a digested protein mixture. The digested protein mixture may comprise other components, for example, undigested protein.

An aspect of the present invention is improved mismatch cleavage due to including in the RNase digestion reaction mixture, crude tryptic or peptic digests of proteins, especially casein, or acid hydrolysates of proteins, especially casein, or yeast extract, or any of a wide variety of other crude amino acid-rich mixtures commonly used in the preparation of bacteriological media. For example, the digested protein mixture may be tryptone, peptone, casamino acids, N–Z amine, yeast extract, an acid or enzymatic hydrolysate of casein, an acid or enzymatic hydrolysate of soy bean, an acid or enzymatic hydrolysate of meat protein, an acid or enzymatic hydrolysate of mixed protein, or brain-heart infusion with peptone and tryptone being more preferred. More preferred embodiments contain digested protein mixtures of casein, yeast, soy bean, meat protein, or other protein, with protein mixtures of an acid or enzymatic hydrolysate of casein being most preferred.

Most of the studies by the inventor used tryptone, a tryptic digest of casein, a protein found in milk although enzymatic hydrolysates of proteins derived from soy beans and meat are also effective. The particular combination of amino acids, short peptides, trace elements, ions, and organic molecules, such as vitamins and co-factors, found in such media, or a particular subset of such components, are highly effective for increasing the extent of specific mismatch cleavage by RNase I in a wide variety of double-stranded RNA targets, and potentially also in RNA/DNA targets. The improved cleavage is most pronounced when the digestion mixture also contains ethidium bromide. The beneficial effect of the protein mixture for improving mismatch cleavage has not yet been seen when RNase T1 is used instead of RNase I, although the presence of this component is not detrimental to mismatch cleavage by RNase T1 and it is reasonable to expect that some effect may ultimately be seen.

The digested protein mixture may be present in a concentration of between about 0.2 and about 100 mg/ml. More preferably, the digested protein mixture is present in a concentration of between about 1 and about 50 mg/ml. In a most preferred embodiment, the digested protein mixture is present in a concentration of between about 10 and about 20 mg/ml.

Fractionation of the crude protein mixture (for example the casein hydrolysate, tryptone, N–Z Amine, yeast extract, etc.) may permit critical components increasing nucleic acid cleaving activity to be identified, allowing the benefits of the present invention to be duplicated using a more well-defined system. However, reconstitution of a defined system may be more difficult, more costly, and no more effective than the present crude mixtures for achieving maximum mismatch cleavage efficiency by RNase I. A detailed analysis of the various components comprising a typical lot of tryptone is included herein to illustrate the factors, including but not limited to ions, vitamins, and co-factors, that are in fact present in this type of crude digested protein mixture (See Table 1).

2. The Divalent Cation Component

A further preferred embodiment of this invention employs a divalent cation as the RNase mismatch cleavage activity enhancing agent although the scientific literature states that divalent cations are not required for RNase I cleavage of single-stranded RNA substrates (Zhu et al., 1990). Indeed, RNase I activity on single-stranded substrates is typically assessed in the presence of the divalent cation-chelating agent, EDTA (Meador and Kennell, 1990; Gesteland, 1966), so that free divalent cations are not present in the RNase I reaction mixture. Quite surprisingly, the present inventor has found that RNase I cleavage of some mismatches is dramatically improved by including certain divalent cations, for example, calcium, manganese, or a combination of calcium and manganese. FIG. 3, FIG. 5A, FIG. 5B, FIG. 5C, FIG. 5D, and FIG. 5E show the effects of $Ca^{++}$. It is likely that other divalent cations will also show this effect.

A more preferred embodiment employs $Ca^{++}$ as the divalent cation. In this embodiment $Ca^{++}$ is preferably present in a concentration of from about 0.1 mM to about 100 mM, with concentrations of from about 0.5 to about 25 mM being more preferred and concentrations of from about 1.5 to about 5 mM being most preferred.

The optimum concentration(s) of divalent cation(s) to use in the RNase digestion mixture may depend on the specific concentrations of the other components, for example, sodium chloride or other monovalent cation(s), ethidium bromide, EDTA, and RNase I. Without being bound by any particular theory, the inventor hypothesizes that the effect of the ions in the reaction is probably due partly to an effect on the RNase and partly to an effect on the target duplex.

3. Useful Intercalating Agents

The invention often takes the form of a reaction mixture having an intercalating agent, for example, ethidium bromide, ethidium homodimer, acridine orange, or Sybr Green™ Of the intercalating agents acridine orange is preferred and ethidium bromide is even more preferred. In preferred embodiments, the intercalating agent is present in a concentration of from about 1 to about 1000 µg/ml. It is more preferred to employ a concentration of intercalating agent of from about 10 to about 100 µg/ml.

Intercalating agents are planar molecules which intercalate between the nucleotide bases in single and double-stranded RNA and DNA. Ethidium bromide is known to those of skill in the art as an intercalating agent that is a sensitive stain for detecting nucleic acids. In the previously mentioned application on the NIRCA™ assay, ethidium bromide was used in the gel and/or electrophoresis buffer, or in a solution in which the gel may be soaked after electrophoresis, for the purpose of detecting the cleavage products under UV light. The role of ethidium bromide in the gel-loading buffer as being potentially effective for increasing the sharpness of the bands (cleavage products) during electrophoresis was also discussed. However, ethidium bromide has never been used as a component of the RNase digestion reaction specifically added to improve mismatch cleavage. Another intercalating agent used to stain nucleic acids, acridine orange, can be also used to improve RNase I cleavage of some base pair mismatches in duplex RNA (FIG. 4).

The finding by the present inventor that intercalating agents, such as ethidium bromide, increase the ability of RNase I to cleave base pair mismatches under certain conditions was unexpected, and not seen with RNase A to the same frequency as is seen for RNase I. The specific mismatch cleavage capability of RNase T1 is also dramatically improved by high concentrations of ethidium bromide (FIG. 2). Unlike the situation with RNase A and RNase I, inclusion of ethidium bromide in the RNase T1 reaction does not require a concomitant reduction in the enzyme level to prevent over-digestion.

Carefully optimized levels of ethidium bromide have so far proven most effective for improving mismatch cleavage. Merely adding ethidium bromide to standard RNase mismatch cleavage reactions using RNase I or RNase A may result in nearly complete non-specific degradation of the target duplex. High levels (higher by about 50–200 fold) of ethidium bromide are needed in one of the preferred embodiments of the present invention (another preferred embodiment uses 25 µg/ml instead of 100 µg/ml), compared to the ethidium bromide concentrations used in the routine detection of nucleic acid (100 µg/ml in the present invention versus 0.5 µg/ml for routine UV detection). The ability to use ethidium bromide at the high levels required for optimal mismatch cleavage, without non-specifically degrading the target duplex, is achieved by a concomitant reduction in the concentration of the RNase (RNase A or RNase I) used for mismatch cleavage.

The mechanism by which intercalating agents, such as ethidium bromide, improves RNase mismatch cleavage is unknown, but probably the effects of ethidium bromide on the mismatched substrate itself are more important than effects on the nucleases. While not wishing to be bound by any particular theory, the intercalation of ethidium bromide into duplex nucleic acid presumably alters its conformation such that mismatches are more susceptible to cleavage. The increased susceptibility may be due to more pronounced helical distortion at the position of the mismatch, to a general loosening of the hydrogen bonds holding the two strands of the duplex together, or even to the recently described phenomenon of "base flipping" (Roberts, 1995). Additionally, ethidium bromide also improves RNase degradation of single-stranded RNA by approximately three times. That is, about one third the amount of the RNase that is required to degrade the single strand substrate in presence of ethanol is required when ethidium bromide is present.

4. Enzymes

The digestion buffers of the present invention allow for a broader choice of enzymes to cleave mismatches. For example, under the standard reaction conditions used in the prior art for performing the RNase digestion step in RNase mismatch cleavage assays, RNase A has heretofore been the only ribonuclease generally thought to be useful for mismatch cleavage.

A preferred embodiment of this invention is a reaction mixture, wherein the RNase enzyme is RNase I, RNase I* from yeast, RNase A, modified RNase A, RNase B, a mixture of RNase A and RNase B, RNase Ti, RNase M, RNase R, RNase E, from the $Rh/T_2/S$ family of RNases (Hime et al., 1995), or the plant nucleases described in Gabryszuk et al., 1995, RNase I is presently most preferred.

The RNase enzyme is typically presently employed in a concentration of from about 0.01 µg/ml to about 500 µg/ml. A concentration of from about 0.1 µg/ml to about 250 µg/ml is even more preferred. Of course, different RNases work best at different concentrations. Most preferred embodiments relevant to specific RNases include a reaction mixtures, wherein the RNase enzyme is RNase A in a concentration of from about 0.01 µg/ml to about 0.5 µg/ml, with the inventors presently employing 0.3 µg/ml; RNase I in a concentration of from about 0.1 μg/ml to about 0.3 μg/ml; or RNase T1 in a concentration of from about 200 μg/ml to about 300 μg/ml, with the inventors presently employing 250 μg/ml.

The advantages of the invention become apparent when looking at the effects of the media on particular RNases.

The present invention allows RNase I to be used for the detection of mismatches. The addition of calcium ions to the RNase I digestion mixture can substitute to a large extent for the protein mixture component, as shown in FIG. 5A, FIG. 5B, FIG. 5C, FIG. 5D, and FIG. 5E, the beneficial effect of the protein mixture can be eliminated by addition of EDTA or EGTA, agents which chelate divalent cations (EDTA) or which preferentially chelate calcium ions (EGTA). Therefore, it is postulated that calcium ion may be one critical component of the protein mixture that confers improved mismatch cleavage by RNase I in some embodiments of the invention. A beneficial effect of divalent cations such as calcium and manganese for mismatch cleavage using RNase A or RNase T1 has not been detected. The inventor has not yet duplicated all of the beneficial effects of a protein mixture component on the cleavage of the broadest range of different mismatches by the mere alternative use of calcium in the RNase digestion mixture. That is, although most mismatches tested which are cleaved by RNase I are cleaved equally well in the presence of optimized levels of calcium and ethidium bromide, compared to optimized levels of tryptone and ethidium bromide, there are some examples of mismatches which are cleaved better in the presence of the tryptone/ethidium bromide mixture.

One particular advantage of the present invention is that it allows for the use of RNase I at much lower concentrations than the methods described in the literature. The amount of RNase I required for optimal cleavage in the present composition is approximately 300–60-fold less than that used in previously described methods. This results in a substantial reduction in the cost of consumable materials needed to carry out the assay. In fact, using the present invention, RNase I appears to surpass RNase A in its ability to cleave base pair mismatches in double-stranded RNA. In contrast, prior studies by the inventor not employing the present invention found that RNase I was inferior to RNase A for mismatch cleavage in both RNA/RNA and RNA/DNA targets. Under the standard RNase digestion reaction conditions used in the prior art, many more of the mismatches in the Factor IX mutants tested in a model system were cleaved by RNase A than were cleaved by RNase I.

RNase T1, isolated from *Aspergillis orysae*, which has not generally been considered a useful enzyme for mismatch cleavage (Myers et al., 1985), is able to specifically cleave many mismatches when used under the conditions of the present invention (FIG. 2). The inventors are aware of only a single instance in the literature that describes RNase T1 being used for cleavage of a basepair mismatch. In that experiment, analysis of the cleavage products was according to the original method (Monchis et al., U.S. Pat. No. 4,946,775, 1990) and not according to the NIRCA™ method presently preferred by the inventors (as described in U.S. patent application SN 08/371,531). Also, that experiment did not employ several of the inventive aspects of the present invention, for instance, no intercalating agent or mismatch cleavage activity enhancing agent such as digested protein or calcium, was used. Marguardt et al., 1991. RNase T1, which is widely known to be specific for cleavage of guanosine residues in single-stranded RNA (see Worthington Enzymes and Biochemicals Manual, 1993, and references therein), had previously been tested for its ability to cleave mismatches containing guanosines in RNA/RNA and RNA/DNA duplexes. No mismatch cleavage was detected previously using this enzyme. That result was in agreement with that of Myers et al. (1985), who also reported that RNase T1 was not able to generate detectable mismatch cleavage products in RNA/DNA targets under various conditions.

Other RNases, namely the cytoplasmic RNase isolated from yeast (Cannistraro and Kennell, 1991) and the bacterial cytoplasmic RNase known as RNase I*, isolated from the cytoplasm of *E. coli*, (Cannistraro and Kennell, 1991) have also been tested and found to be capable of cleaving single base pair mismatches in duplex RNA, and potentially also in RNA/DNA duplexes, especially when used in conjunction with the other novel reaction components of the present invention. It is likely that other bacterial RNases, for example, the periplasmic RNase isolated from *Aeromonas hydrophila* (Favre et al., 1993), will also be useful for mismatch cleavage in the reaction mixtures of the present invention.

Although not all known eukaryotic and prokaryotic ribonucleases have been tested for improved ability to cleave mismatches when used according to the present invention, the advantages of the present invention are expected to be general, because the activity of all RNases which have been tested (both eukaryotic and prokaryotic) have been found to be improved.

One of the most important aspects of the RNase digestion conditions disclosed in the present invention is that they result in a significantly higher mutation detection rate than has been previously reported using the RNase mismatch cleavage assay. Detection is improved by using RNases which do not reliably cleave base pair mismatches under standard conditions. RNases found to be especially improved by the present invention in their ability to cleave mismatches include RNase I and RNase T1. However, the invention reduces the amount of non-specific cleavage seen with RNase A, and reduces the amount of RNase A needed for specific cleavage, when RNase A is used in the mismatch cleavage assay.

Of the three mutations in the Factor IX model system that were not detected by either RNase A alone or the RNase A/RNase I combination used in the initial studies, all are detected using the new RNase digestion conditions disclosed in the present invention. Mutations in the p53 tumor suppressor gene that are not detected by RNase A are also detected by RNase I using the new conditions (FIG. 6A, FIG. 6B, and FIG. 6C). Moreover, when the entire panel of 60 mismatches in the model system (2 complementary mismatches are generated from each of the 30 point mutations) is compared using the new RNase digestion components and the components used in the method described in U.S. patent application Ser. No. 08/371,531, it is clear that the new conditions show a dramatic improvement in the general ability to specifically cleave a wide variety of mismatches.

There are some examples of mismatches which are cleaved better by RNase A than RNase I, when the conditions of this invention are used. Part of the general improvement seen in the RNase mismatch cleavage assay using the conditions disclosed herein is due to the reduction in non-specific cleavage seen when using RNase I instead of RNase A. Even when RNase A is used instead of RNase I, the background of non-specific cleavage is reduced by using the RNase digestion reaction components specified in the present invention. Therefore, a general property of the invention seems to be the ability to reduce the effects of non-specific background cleavage. This results in a lower background and improved signal-to-noise ratio in the assay. The general reduction in non-specific cleavage can make it feasible to mix together two or more RNases (e.g., RNase A and RNase I) to use in mismatch cleavage assays. This would reduce the labor involved (compared to using the RNases in separate readiness) and potentially improve cleavage of some mismatches.

5. Other Components

Another embodiment of the invention encompasses a reaction mixture that further comprises NaCl. When employed the sodium chloride is preferably present in a concentration of from about 5 to about 300 mM. A concentration of from about 50 to about 200 mM is more preferred, with a concentration of from about 15 to about 100 mM being most preferred.

The reaction mixture may also contain additional ingredients, for example sodium chloride, Tris-buffer, EDTA, etc. These components may be useful for achieving optimal sensitivity and specificity of mismatch cleavage. For example, if the NaCl concentration falls below a threshold level, non-specific cleavage increases dramatically, especially when RNase A or RNase I is used. This effect can be counteracted by reducing the ribonuclease concentration. Adding ethidium bromide to a reaction previously balanced for NaCl and RNase concentration can also increase non-specific cleavage dramatically, especially when the RNases used are RNase I and/or RNase A.

The optimal concentration of the digested protein component tends to be more constant between reactions that differ widely in the levels of NaCl, RNase, and ethidium bromide. Because optimal levels of the reaction components vary depending on the concentrations of other components, two different examples of compositions containing the digested protein mixture are provided of some of the preferred embodiments of the invention for illustrative purposes only. In one composition, the monovalent cation (NaCl) has been eliminated, although residual sodium (about 20 mM) is provided by the predigested protein (i.e., tryptone) component.

6. Nucleic Acids

The reaction mixture of the present invention typically further comprises a nucleic acid. The nucleic acid may be a double stranded nucleic acid. The double stranded nucleic acid may be a double stranded RNA, an RNA/DNA duplex or a double stranded DNA. Most NIRCA™ based aspects of the invention employ a double stranded RNA.

B. NUCLEIC ACID DIGESTION BUFFERS

Another aspect of this invention is a nucleic acid digestion buffer comprising a protein mixture. As used herein the term "nucleic acid digestion buffer" refers to a mixture of components capable of cleaving a nucleic acid. Preferred embodiments of this invention encompass nucleic acid digestion buffers that allow specific RNase cleavage of base pair mismatches and are thus useful for detecting point mutations. The nucleic acid digestion buffer is preferably further defined as an RNA digestion buffer. An even more preferred embodiment encompasses a RNA digestion buffer that is further defined as being adapted for cleavage of base pair mismatches in an RNA/DNA duplex or, most preferably, in double stranded RNA.

A preferred embodiment of this invention encompasses a nucleic acid digestion buffer, wherein the protein mixture is a digested protein mixture. A more preferred embodiment encompasses employing tryptone, peptone, casamino acids, N–Z amine, yeast extract, an acid or enzymatic hydrolysate of casein, an acid or enzymatic hydrolysate of soy bean, an acid or enzymatic hydrolysate of meat protein, or an acid or enzymatic hydrolysate of mixed protein as the digested protein mixture. Even more preferred embodiments use tryptone or peptone as the digested protein mixture. A further preferred embodiment is a nucleic acid digestion buffer, wherein the digested protein mixture is an acid or enzymatic hydrolysate of casein, soy bean, meat protein, or mixed protein. At presently, most preferred embodiments employs a pancreatic digest of casein—tryptone.

Although the identity of the protein mixture will affect its optimal concentration, it is generally preferable to employ a nucleic acid digestion buffer, wherein the protein mixture is present in a concentration of between from about 0.2 to about 100 mg/ml. Concentrations of protein mixtures between about 1 and about 50 mg/ml are more preferred and between about 10 and about 40 mg/ml are the most preferred. The inventors presently employ 32 mg/ml in a stock buffer, which is diluted to 25.6 mg/ml during the preparation of the final reaction mixture for an assay.

A preferred embodiment encompasses a nucleic acid digestion buffer which further comprises an intercalating agent. The intercalating agent is preferably ethidium bromide, ethidium homodimer, acridine orange, or Sybr Green™, with acridine orange being more preferred and ethidium bromide being the most preferred. The intercalating agent is preferably present in concentrations as described previously for reaction mixtures of this invention.

Another preferred embodiment encompasses a nucleic acid digestion buffer, further comprising an RNase enzyme. Preferred RNase enzymes for nucleic acid digestion buffers are typically those employed in reaction mixtures of this invention as described above.

C. METHODS OF CLEAVING AND DETECTING BASE PAIR MISMATCHES

Another aspect of this invention encompasses a method for detecting a base pair mismatch in a nucleic acid molecule; comprising the steps of: obtaining a single stranded RNA test sample to be analyzed; contacting said RNA test sample with a single stranded nucleic acid probe thereby forming a test duplex; treating said test duplex with a ribonuclease composition capable of cleaving double-stranded RNA molecules containing base pair mismatches under conditions effective to allow the formation of cleavage products, said ribonuclease composition comprising: (1) an RNase enzyme; (2) a nucleic acid intercalating agent; and (3) an RNase mismatch cleavage activity enhancing agent comprising a protein mixture—preferably a digested protein mixture, a divalent cation, or both; and separating said cleavage products under conditions that allow the cleavage products to remain double-stranded.

1. The Test Nucleic Acid Duplex

The "test nucleic acid duplex" is a double stranded nucleic acid that is to be assayed for the presence of base pair mismatches. For example, this is the sample to be screened for mutations if this method were employed to screen patients for various diseases or conditions characterized by nucleic acid mutations. The double stranded nucleic acids, RNase mismatch cleavage activity enhancing agents, RNase enzymes, and intercalating agents employed in this aspect of the invention are as described previously.

2. RNA Test Sample

In this aspect of the invention the RNA test sample is reacted with a nucleic acid probe, typically of known nucleic acid sequence and preferably a single stranded RNA, such that a nucleic acid duplex is formed by complementary interactions between base pairs. The ribonuclease composition of this aspect should be designed to specifically cleave base pair mismatches. Therefore, reacting the nucleic acid duplex with the ribonuclease that cleaves at mismatches allows for the determining of mismatches between the test sample and the nucleic acid probe. This provides a method for detecting mutations in the RNA test sample. The elements of the preferred ribonuclease composition is as described previously for reaction mixtures and nucleic acid digestion buffers of this invention.

In preferred embodiments of this aspect, the RNA test sample and RNA probe are prepared by transcription of a recombinant plasmid or a PCR product. It is even preferable to prepare the RNA test sample and RNA probe simultaneously in the same reaction by in vitro transcription.

The RNA test sample may be purified from a cellular extract or obtained from a biological sample from a patient suspected of having a disease associated with a genetic mutation. To screen for genetic diseases, an RNA transcript from a normal gene ("probe") is hybridized to an RNA transcript from the test gene (i.e., from a patient sample), to form a duplex RNA target molecule. Regions of non-complementarily between the probe and the test transcripts will result in base pair mismatches of one or more bases in the duplex RNA target molecule. The target molecule is then reacted with a mixture comprising an RNase capable of cleaving unpaired residues ("mismatched") in the target molecule, and agents which enhance the ability of the RNase to effect said cleavage. The cleavage products are separated according to size by electrophoresis or other means and analyzed by comparison to cleavage products from a control duplex RNA molecule ("no-mismatch control") produced by hybridizing of complementary transcripts from the normal gene and similarly treated with RNase. Differences in the sizes of the cleavage products are indicable of mutations in the target molecule. The size differences are due to cleavage by RNase at the regions of non-complementarily between the normal transcript and the transcript from the test gene. The regions of non-complementarily are due to mutations in the test gene.

3. Separation of Cleavage Products

A preferred embodiment of this aspect includes separating the cleavage products using non-denaturing gel electrophoresis. The cleavage products may preferably be admixed with a high ionic strength loading solution to form a loading sample prior to separation by non-denaturing gel electrophoresis. In even more preferred embodiments the loading solution comprises a salt in a concentration sufficient to provide a final salt concentration in each loading sample of at least about 0.5 M. The loading solution preferably comprises a tetramethyl alkyl salt, such as is tetramethylammonium chloride, or NaCl.

Alternatively, it may be preferable to separate the cleavage products using non-denaturing HPLC or capillary electrophoresis.

4. Detection of Cleavage Products

The cleavage products may be detected by methods known of skill in the art. For example, they may be contacted with an agent that causes the cleavage products to fluoresce, such as ethidium bromide. This agent may be incorporated into the nondenaturing gel or added to the sample prior to electrophoresis. The cleavage products may also be analyzed by silver staining or using an automated device.

D. METHODS FOR IDENTIFYING A MUTATION IN A GENE

Another embodiment of the present invention is a method for identifying a mutation in a gene; comprising the steps of: obtaining a single stranded RNA test sample from said gene and a single stranded RNA non-mutant control sample having the wild type sequence of said gene; contacting said test RNA sample and said non-mutant control RNA sample with a single stranded RNA probe, thereby forming a test RNA duplex and a control RNA duplex; treating said test RNA duplex and said control RNA duplex with a ribonuclease composition capable of cleaving double-stranded RNA molecules containing base pair mismatches, under conditions effective to allow the formation of cleavage products, said ribonuclease composition comprising: (1) an RNase enzyme; (2) a nucleic acid intercalating agent; and (3) an RNase mismatch cleavage activity enhancing agent comprising a digested protein mixture, a divalent cation, or both; separating said cleavage products under conditions that allow the cleavage products to remain double-stranded; and comparing the separated cleavage products from said test RNA duplex and said control RNA duplex, wherein a difference in the size of the cleavage products is indicative of the presence of a mutation in said gene.

Preferred ribonuclease compositions have been described previously. The single stranded RNA probe may have a sequence of the wild type gene and thus form a duplex with said control sample that does not contain a mismatch. It may also have a sequence of the mutant gene and thus form a duplex with said control sample that contains a mismatch. The single stranded RNA test sample is preferably obtained from a patient suspected of having a disease associated with a genetic mutation, such as cancer. A preferred embodiment of this invention employs a p53 gene.

E. KIT FOR DETECTING BASE PAIR MISMATCHES

An embodiment of this invention is a kit for use in conducting an RNase protection assay, the kit comprising, in a suitably aliquoted form, a means of generating RNA and an RNA digestion buffer comprising a digested protein mixture, a divalent cation, or both and an intercalating agent. The preferred RNA digestion buffers are as previously described for reaction mixtures and nucleic acid digestion buffers.

The means of generating RNA may preferably comprise a first and second PCR primer, each primer including a promoter sequences and a gene sequence from spatially separated regions of the same gene, and a RNA polymerase interactive with said promoter. The means for generating RNA further comprises a second RNA polymerase interactive with said second promoter. An even more preferred embodiments include having the means of generating RNA further comprise a transcription buffer and a nucleotide solution. The means of generating RNA may further comprise a template gene sequence having the wild type sequence of said gene and a template gene sequence having the mutant sequence of said gene.

The term promoter will be used here to refer to a group of transcriptional control modules that are clustered around the initiation sites for the RNA polymerases. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation. The phage promoters, being small, of a single subunit, stable, and easy to produce are useful in the invention.

F. A KIT FOR USE IN DETECTING SINGLE BASE CHANGES IN A NUCLEIC ACID SEQUENCE

Further aspects of the invention concern kits for use in RNase protection assays. Such kits will generally have as one component an enzyme or enzymes capable of cleavages of base pair mismatches and capable of detecting single base mismatches in an RNA/RNA duplex. These enzymes will be employed in the inactive reaction conditions of the present application.

The enzyme or enzymes may be provided in lyophilized, powdered form to be stored in a freezer at about −20° C. to about −80° C. and to be mixed with solvents in the indicated concentrations just prior to use, or alternatively, the enzyme or enzymes may be provided in solution in an appropriate buffer and possibly glycerol solution. All of the said solvents and buffers may or may not be provided with the kit.

The kits will generally also contain a high ionic strength gel-loading solution for use in significantly enhancing the resolution of the RNase cleavage products. Such a solution will contain, in addition to the standard components, a concentration of a salt sufficient to retard and to focus double-stranded RNA fragments into sharp bands. Suitable salts are sodium chloride and tetramethylammonium chloride (TMAC). An example of a high ionic strength gel-loading solution is 3 M TMAC, 10 mM Tris 7.5, 2 mM EDTA, 0.1% bromophenol blue, 50% glycerol. The buffer may be provided as a premixed solution or as various aliquots of components for forming such a solution.

Other components of the kit may include, but are not limited to, components for preparing a non-denaturing gel, a solution of enzyme buffer and/or a solution of NaCl. Sterile, nuclease free, purified water may also be included in the kit. The kit may also contain a control RNA template(s) with and/or without a mismatch with a complementary RNA probe. The RNA molecules will be provided in solution or in lyophilized form and would be stored at 4° C. or alternatively could be stored at −20° C. to −80° C.

The kit may also contain PCR primers to be used to amplify the test sample. The primers will preferably be comprised of phage promoter sequences to be used in the transcription of the PCR products. The primers may also comprise sequences complementary to the regions of test sample being amplified. The phage promoter sequences are appended to the 5' ends of the test gene-specific sequences.

A specific example of a kit in accordance with the invention is that which includes a 10X transcription buffer and rNTP mix; SP6 and T7 RNA polymerases (20 Units/ml each); a hybridization solution; an RNase stock solution and digestion buffer; the afore-mentioned improved gel loading solution; RNase-free dH$_2$O; a wild type and mutant control template, e.g., for the p53 gene; and PCR primers (amplimers) with phage promoters.

G. METHODS OF SCREENING FOR AN RNase MISMATCH CLEAVAGE ACTIVITY ENHANCING AGENT Another embodiment of the present invention is a method of screening for an RNase mismatch cleavage activity enhancing agent comprising: obtaining a digested protein mixture; fractionating the digested protein mixture into two or more fractions; and testing a fraction of the digested protein mixture for RNase mismatch cleavage activity enhancing characteristics. Preferred digested protein mixtures are as described previously for other embodiments of this invention.

A preferred embodiment of this invention is the method of screening for an RNase mismatch cleavage activity enhancing agent, wherein the step of testing the fraction comprises: preparing a test RNA digestion buffer comprising the fraction and an RNase enzyme; preparing a control RNA digestion buffer substantially identical to the test RNA digestion buffer and comprising the same RNase enzyme, but not having the fraction; performing parallel tests with both the test RNA digestion buffer and the control RNA digestion buffer to determine the relative activities of the RNase enzyme in the test and control buffers. Preferred RNase enzymes in the practice of this aspect of the invention are as described previously.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Cleavage of mismatches using prior art and current invention compositions for RNase I digestion buffer.

FIG. 5 is composed of five panels: FIG. 5A, FIG. 5B, FIG. SC, FIG. 5D, and FIG. 5E.

FIG. 6 is composed of three panels: FIG. 6A, FIG. 6B, and FIG. 6C.

FIGS. 7A–7B: Cleavage of mismatches in a large panel of homozygous and heterozygous samples with Factor IX mutations. FIG. 7 is composed of two panels: FIG. 7A and FIG. 7B.

DETAILED DESCRIPTION OF SPECIFIC EMBODIMENTS AND EXAMPLES

A. Detailed Description

Figure 2:
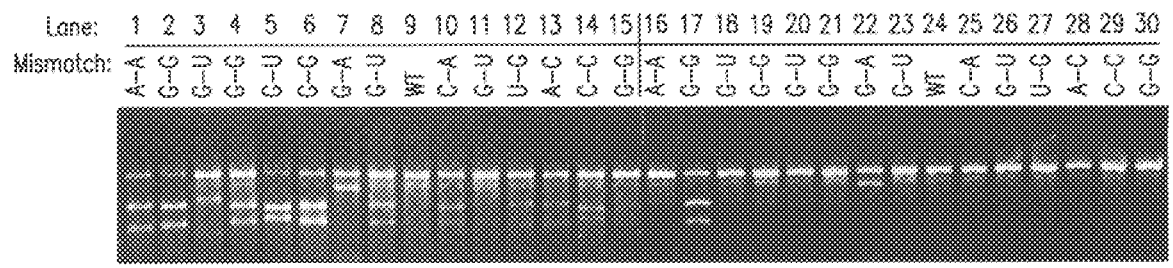
FIG. 2: Cleavage of mismatches using RNase T1.

The present invention arises from the discovery of improved compositions and methods of mismatch detection in the RNase protection assay. The improvement lies in the use of intercalating agents, divalent metal ions and elements of a protein mixture in the reaction mixtures. Through the use of these improved methods and compositions, marked improvement is seen. The compositions are effective for specific cleavage of base pair mismatches in double-stranded nucleic acid, and especially in double-stranded RNA targets.

In its most preferred embodiment, the present invention comprises ribonucleases such as RNase I, RNase T1, and RNase A used alone or in combination, in a reaction mixture comprising (a) an intercalating agent; (b) certain divalent cations and/or a digested protein mixture.

1. Preferred Enzymes

The enzyme may be RNase I isolated from *E. coli*, or may be another *E. coli* enzyme with similar properties and substrate specificity. It may also be isolated from other prokaryotes, eukaryotes, yeast, fungi, or other organisms. It should be present at a concentration to effect optimal specific cleavage of said mismatches, when admixed with the other reaction components. More particularly, RNase I may be present in the reaction mixture at a concentration of from about 0.1 to about 0.5 units per microliter. This concentration is from about 300 to about 60-fold lower than that recommended previously in the art.

One unit of RNase I may be defined as the amount needed to cause 50% degradation of a radiolabeled single-stranded RNA substrate mixed with 2 micrograms of yeast RNA in 30 minutes at 37° C., as determined by trichloroacetic acid precipitation (Ambion unit definition). Alternatively, one unit of RNase I may be defined as the amount required for complete degradation of 2 micrograms of *E. coli* 5S ribosomal RNA in 5 minutes at 37° C. (Promega definition). The conversion between Ambion and Promega units of RNase I is thus 12 Ambion units equals approximately one Promega unit, since a Promega unit degrades twice as much substrate (2 micrograms versus 50% of 2 micrograms) in one-sixth the time period (5 minutes versus 30 minutes).

The enzyme known as RNase YI*, isolated from yeast, is also effective for cleaving base pair mismatches in duplex RNA when used in conjunction with the ethidium bromide and protein mixture components of the RNase digestion reaction mixture. This enzyme is not commercially available and a strict unit definition of its activity has not been established. It was used at final concentrations ranging from 1:30 to 1:300 dilutions of the stock preparation supplied by Dr. David Kennell. This enzyme is typically used in a concentration necessary to degrade 10 mg poly C to 1–5 mM in 30 min. at 37° C. The enzyme is usable in a buffer of 20 mM TRIS (pH 7.3–7.7), 10 mM $Mg^{2+}$ or 0.1 mM $Zn^{2+}$, and 0.5 mM EDTA.

Another preferred embodiment of the present invention encompasses using the fungal RNase, RNase T1, to effect double-strand cleavage of mismatches in duplex RNA targets. The RNase T1 may be isolated from the fungus *Aspergillus orysae* or other Aspergillus species or from suitable bacterial host strains overexpressing the cloned fungal gene. The RNase T1 may be present at a concentration of about 100–250 micrograms/ml, corresponding to a unit concentration of about 64,000–160,000 units/ml (where 25 units are defined as the amount of RNase T1 required to degrade 25 micrograms/ml of a GpA dinucleotide substrate to cause an absorbance change of 0.01 $A_{260}$ units in one minute at room temperature, in a reaction mixture containing 50 mM Tris-Cl, pH 7.5, mM EDTA; Ambion definition).

Although RNase T1 was previously reported not to be able to cleave base pair mismatches under various reaction conditions (Myers et al., 1985), the inventor has found that a wide variety of different mismatches are in fact cleaved by this enzyme under the appropriate conditions, to generate double stranded cleavage products from duplex RNA test substrates containing single-base mismatches. In order to achieve optimal mismatch cleavage using RNase T1, high enzyme levels may be used (for example, 64,000–160,000 units/ml in the standard reaction described in Example 1), and the reaction mixture may also contain high concentrations of ethidium bromide or other intercalating agent(s), for example 100 µg/ml ethidium bromide. However, lower RNase T1 concentration and/or lower ethidium bromide concentrations are also effective for cleaving many mismatches. Some mismatches which are partially cleaved using lower RNase T1 and/or lower ethidium concentrations, may be more completely cleaved when the concentrations of these components are raised.

The protein mixture component of the RNase digestion mixture, which is required for maximal mismatch cleavage activity by RNase I, does not appear to be required for RNase T1, at least not in the specific mismatches tested thus far. The ability of RNase T1 to effect double-strand cleavage of base pair mismatches in RNA duplexes is surprising, given the reported specificity of RNase T1 for cleavage after guanosine residues only, in single stranded RNA substrates (Worthington enzyme manual, 1993; enzyme 3.1.27.3, described on page 359).

The RNase A used for mismatch cleavage in the present invention may be isolated from bovine pancreas or from pancreas of other mammalian species, or may be one of a large family of related RNases isolated from other mammalian organs or sources (for example, brain or serum), or may be a genetically altered RNase A analog, such as those described by Raines and del Cardayre, U.S. Pat. No. 5,389, 537. The RNase A may be present at a concentration of about 0.1–0.5 micrograms/ml. This concentration is about 400-fold lower than the amount historically used in the RNase protection assay. Historically, preferred concentrations of RNase A to be used for mismatch cleavage have been given in units of mass, rather than activity (Myers et al., 1985; Maniatis et al., U.S. Pat. No. 4,946,773). The mass amount of RNase A used may be converted to units of activity defined as follows (Ambion unit definition): one unit of RNase A is the amount needed to give an increase in absorbance at 286 nm of 0.0146 units per minute, when incubated with 1 mM cyclic CMP substrate in a volume of 1 ml.

Preferred embodiments of the present invention also include the cleavage of base pair mismatches using RNases isolated from other eukaryotic or prokaryotic sources. These alternate RNases may be used to effect cleavage, especially double-stranded cleavage, of base pair mismatches in duplex nucleic acid targets. Since the methods disclosed herein have been shown to be effective with RNases previously reported to be incapable of mismatch cleavage (i.e., RNase T1) or previously not used or not widely used for mismatch cleavage (i.e., RNase I from *E. coli*, RNase Y1* from yeast), it is contemplated that other RNases and perhaps other endonucleases not heretofore known to be capable of effecting mismatch cleavage may in fact be useful for this purpose.

These potentially useful nucleases include, but are not limited to, S1 nuclease, mung bean nuclease, any or all of the RNases in the large family of ribonucleases related to RNase A (see Jermann et al., 1995), RNase T2, the broad specificity RNase from *Aeromonas hydrophila* (which is related to RNase I from *E. coli*; Favre et al., 1993), RNase E from *E. coli* (McDowall et al., 1994) and RNases encoded in the

*Drosophila melanogaster* genome (Hime et al., 1995). RNases made by random or site-directed mutagenesis of natural RNase genes, for example the RNase A-derived enzymes described by Raines and del Cardayre (U.S. Pat. No. 5,389,537 and references therein), are also expected to be useful for mismatch cleavage when used according to the methods set forth in the present disclosure.

2. Preferred Protein Mixtures

This invention also teaches the use of a protein mixture to enhance specific base pair mismatch cleavage. The protein mixture is preferably pre-digested, such as an acid hydrolysate or enzymatic digest of casein protein, soy bean protein, meat protein, or mixed protein, or a crude extract containing such pre-digested protein components (for example, yeast extract). Enzymatic digests of such proteins may consist of digests with trypsin or pepsin. Such pre-digested proteins (for example, tryptone, peptone, casamino acids, N–Z amine) are commonly sold as bacteriological media. These products may contain a mixture of amino acids, short peptides, ions, trace elements, and organic molecules, such as vitamins and co-factors.

A typical analysis of one such digested protein mixture, tryptone, which has been shown to be particularly useful in the present invention, is included herein in Table 1.

TABLE 1

ANALYSIS OF TRYPTONE - A PANCREATIC DIGEST OF CASEIN

| ANALYTE | RESULTS |
|---|---|
| Physical Characteristics | |
| Ash (%) | 6.8 |
| Clarity, 1% Solution (NTU) | 0.5 |
| Filterability (g/cm$^2$) | 1.3 |
| Loss on Drying (%) | 3.7 |
| pH, 1% Solution | 7.2 |
| Carbohydrate (%) | |
| Total | 7.7 |
| Nitrogen Content (%) | |
| Total Nitrogen | 13.0 |
| Amino Nitrogen | 5.2 |
| AN/TN (%) | 40.0 |
| Amino Acids (%) | |
| Alanine | 2.86 |
| Arginine | 3.03 |
| Aspartic Acid | 6.11 |
| Cystine | 0.42 |
| Glutamic Acid | 17.05 |
| Glycine | 1.75 |
| Histidine | 2.02 |
| Isoleucine | 4.40 |
| Leucine | 7.11 |
| Lysine | 6.70 |
| Methionine | 2.57 |
| Phenylalanine | 3.71 |
| Proline | 7.45 |
| Serine | 4.29 |
| Threonine | 3.58 |
| Tryptophan | 0.71 |
| Tyrosine | 1.42 |
| Valine | 5.00 |
| Inorganics (%) | |
| Calcium | 0.013 |
| Chloride | 0.186 |
| Cobalt | <0.001 |
| Copper | <0.001 |

TABLE 1-continued

ANALYSIS OF TRYPTONE - A PANCREATIC DIGEST OF CASEIN

| ANALYTE | RESULTS |
|---|---|
| Iron | <0.001 |
| Lead | <0.001 |
| Magnesium | 0.017 |
| Manganese | <0.001 |
| Phosphate | 2.669 |
| Potassium | 0.229 |
| Sodium | 2.631 |
| Sulfate | 0.241 |
| Sulfur | 0.740 |
| Tin | <0.001 |
| Zinc | 0.003 |
| Vitamins (ug/g) | |
| Biotin | 0.1 |
| Choline (as Choline Chloride) | 350.0 |
| Cyanocobalamin | <0.1 |
| Folic Acid | 0.3 |
| Inositol | 1400.0 |
| Nicotinic Acid | 97.8 |
| PABA | 3.7 |
| Pantothenic Acid | 5.3 |
| Pyridoxine | 0.6 |
| Riboflavin | <0.1 |
| Thiamine | 0.4 |
| Thymidine | 93.4 |
| Biological Testing (CFU/g) | |
| Coliform | negative |
| Salmonella | negative |
| Spore Count | 73 |
| Standard Plate Count | 870 |
| Thermophile Count | 8 |

The list of components includes ions such as calcium, cobalt, iron, manganese, magnesium, copper, sulfur, tin, and zinc. Tryptone also typically contains vitamins, such as biotin, choline, folic acid, inositine, pyridoxine, thiamine, and riboflavin, and also co-factors such as nicotinic acid. Many of these molecules contain planar groups which may be capable of intercalating into double-stranded nucleic acid and altering its cleavage susceptibility.

Although preferred embodiments of this invention encompass employing tryptone as the protein mixture, this invention also incudes the use of a protein mixture other than tryptone. The inclusion of any of several different components normally used in the preparation of bacteriological growth media has been shown by the inventor to increase the ability of RNase I to effect double-strand cleavage of mismatches in duplex RNA substrates. For example, media other than tryptone which provide the beneficial effect include yeast extract (used at a concentration of about 5–15 mg/ml), case in hydrolysate, which is an acid hydrolysate of the milk protein casein (used at a concentration of about 10–30 mg/ml), N–Z Soy Peptone, Casein N–Z Amine, and Primatone, all products of Difco Laboratories, Detroit, Mich., and all used at similar concentrations to tryptone, i.e., 10–30 mg/ml.

The protein mixture may be added to the reaction mixture at an optimal concentration to increase the ability of RNases to effect specific cleavage of base pair mismatches, when admixed with the other reaction components. More particularly, the protein mixture may be present at similar or somewhat higher concentrations as those used for the growth of bacteria in culture, that is, from about 10 to about 40 mg/ml.

3. Preferred Divalent Cations

Another surprising aspect of this invention is the ability of divalent cations to enhance the specific cleavage of mutations when employing RNase I. The divalent cations in the reaction mixture should be present at an optimal concentration to increase the ability of RNase I to effect specific cleavage of base pair mismatches, when admixed with the other reaction components. More particularly, calcium may be present at a concentration of from about 0.5 mM to about 10 mM. Other divalent cations, for example manganese, may be able to substitute partly or completely for calcium. This result is unexpected since RNase I does not require divalent cations for activity according to the scientific literature. (Zhu et al., 1990).

4. Preferred Intercalating Agents

Another novel aspect of this invention is the increased ability to detect mutations via the addition of an intercalating agent. The intercalating agent is preferably ethidium bromide or a similar intercalating compound, for example, ethidium homodimer or acridine orange. The intercalating agent should be present in the reaction mixture at an optimal concentration to increase the ability of RNases to effect specific cleavage of base pair mismatches, when admixed with the other reaction components. More particularly, ethidium bromide may be present at a concentration of from about 25 to about 100 $\mu$g/ml. This concentration is about 50–200-fold higher than the concentration (0.5 $\mu$g/ml) typically used to stain double-stranded nucleic acids for UV detection.

Embodiments of this invention also encompass using intercalating agents other than ethidium bromide. For example, specific cleavage of base pair mismatches in duplex RNA is improved by the inclusion of acridine orange, a common nucleic acid stain which intercalates between the bases in double-stranded RNA, in the RNase digestion mixture. Acridine orange was added at concentrations ranging from about 5 $\mu$g/ml to about 20 $\mu$g/ml, and shown to improve cleavage in 4 of the 5 mismatches tested. The fifth mismatch was cleaved even in the absence of an intercalating agent. See FIG. 4. One may also use intercalating agents such as ethidium homodimer, Sybr Green I™, and Sybr Green II™ (available from Molecular Probes, Inc. or through FMC Biotechnology Corp.) for this purpose. The preferred concentration of the various intercalating agents in the RNase digestion reactions may vary depending on the specific agent used, but will generally fall in the range of about 0.5–50 $\mu$g/ml.

5. Examples of Reaction Mixtures

A general composition for a mixture effective for cleaving base pair mismatches in duplex nucleic acid targets would contain an RNase with specificity for single-stranded regions of duplex RNA targets; an intercalating agent present at 0.5–50 $\mu$g/ml; and a mismatch cleavage activity enhancing agent such as a digested protein mixture and/or calcium ion. The digested protein mixture may contain trade contaminants which are effective for providing the mismatch cleavage activity enhancing agent. The composition may also contain additional ingredients such as sodium chloride or other monovalent cations, formamide, Tris buffer or other physiological buffer, detergents such as SDS, magnesium ion, or other components carried over from the in vitro transcription reaction used to produce the transcripts that are hybridized to make the duplex RNA target.

A specific example of a reaction mixture of the present invention may contain the following components: tryptone (preferably about 25 grams/liter); ethidium bromide (preferably about 25 micrograms/ml); sodium chloride (preferably about 85 millimolar), and RNase I (preferably about 0.5–1 unit/microliter), or RNase A, (preferably at a concentration of about 0.5 nanograms/microliter), or RNase T1 (preferably at about 64–160 units per microliter). Instead of tryptone, the reaction mixture may contain calcium chloride (preferably about 1.5–10 millimolar).

Alternatively, the reaction mixture may contain: tryptone (preferably about 25 grams/liter); ethidium bromide (preferably about 80 micrograms/ml); and RNase I (preferably from about 0.1 unit to about 0.33 units per microliter), or RNase A, preferably at about 0.1 nanograms per microliter, or RNase T1 (preferably at about 64–160 units per microliter). A "digestion reaction" is usually prepared by a user from a stock nucleic acid digestion buffer solution which is diluted during preparation of the reaction mixture. The inventor currently envisions that a commercial stock buffer solution might comprise 100 $\mu$g/ml ethidium bromide and 32 mg/ml tryptone, which will be diluted to final concentrations of 80 mg/ml and 25.6 mg/ml, respectively, during the preparation of the digestion reaction.

For cleavage of base pair mismatches by RNase T1, the above reaction mixtures may be used, or the tryptone or digested protein or calcium ion component may be omitted from the reaction mixture. The requirement for the digested protein or calcium ion component for optimal cleavage of mismatches with RNase I does not appear to apply to RNase T1, at least not with those mismatches tested thus far. It is possible that examples will be found in the future of mismatches which are cleaved better by RNase T1 when the digested protein and/or calcium ion components are included in the reaction mixture. The RNase T1 may be present at a concentration of about 64–160 units per microliter, corresponding to a mass concentration of about 100–250 micrograms per milliliter. The preferred concentration of ethidium for mismatch cleavage by RNase T1 is from 25–100 micrograms per milliliter, especially 100 $\mu$g/ml.

In a preferred embodiment, one volume of solution containing the double-stranded nucleic acid substrate may be mixed with four volumes of one of the above mixtures and incubated for 30–60 minutes at 370° C. After the incubation, gel-loading buffer may be added and the RNA cleavage products may be analyzed by the NIRCA™, techniques described in the previously mentioned patent application.

The concentrations of each of the above reaction components may generally be varied over at least a several-fold range and still provide an effective composition for cleavage of base pair mismatches in double-stranded RNA and presumably also in RNA/DNA targets. Although cleavage of base pair mismatches in DNA/DNA targets would not be expected to occur using RNases, it is possible that this invention may also improve cleavage of such mismatches by DNases or non-specific nucleases such as S1 or mung bean nuclease.

In some cases, the concentrations of the above components may be varied independently over appropriate ranges. For example, the digested protein and calcium components may be varied over a several-fold range from that stated in the preferred embodiment, and still provide an effective concentration for improving mismatch cleavage by RNases.

For other components, varying the concentration of certain components may require that the concentration(s) of other components be varied concurrently to maintain the optimal composition for specific mismatch cleavage. For example, the RNase I concentration may be increased to 5 units/microliter, and the ethidium bromide concentration concurrently decreased to about 10 micrograms/milliliter, while still providing a composition effective for the specific cleavage of base pair mismatches in duplex RNA targets. If the RNase I concentration is increased beyond about 5 units/microliter, the ethidium bromide concentration must be further decreased in order to prevent non-specific digestion of the target duplex. If the sodium chloride and/or EDTA concentrations are increased or decreased, the concentrations of ethidium bromide and/or tryptone and/or calcium and/or RNase enzyme (especially RNase I and/or RNase A) may be adjusted to compensate for the resulting altered stability of the target duplex, and the resulting altered concentrations of monovalent cation in the reaction mixture.

The optimal levels of the various reaction components may also be dependent on the nucleotide composition and sequence of the specific target region being analyzed. For example, higher RNase I levels and/or lower sodium chloride levels may be required for cleaving mismatches in G+C-rich targets, compared to A+U-rich targets.

6. Amplification of Target Regions

The present invention may be useful for detecting mutations in nucleic acid sequences obtained by amplification of a target region by a variety of methods. These methods include amplification by PCR of genomic or mitochondrial DNA, amplification of mRNA or viral RNA by reverse transcriptase (RT)-PCR, or amplification from recombinant plasmids, phagemids, bacteriophage, or artificial yeast or human chromosome vectors and other methods known in the art.

The methods disclosed herein may have particular utility in the amplification of target regions from test and control samples from genomic DNA, cloned DNA, previously amplified DNA, or RNA. A particularly preferred method is the PCR, with incorporation of exogenous promoter sequences into the amplified product by including phage promoter sequences in the oligonucleotide primers used in the amplification reaction. The promoter sequences are added in such a way that both strands of the amplified product can be transcribed into RNA in vitro. That is, promoter sequences are added to the 5' ends of both the forward and the reserve PCR primers. The promoter sequences may be the same or different.

The target region may also be amplified from expressed sequences in test and control samples from mRNA isolated from a cell, mRNA transcribed in vitro, or from viral RNA. The test samples may be tumor tissue and the expressed sequences those from somatically mutated genes, or the test samples may be normal tissue with sequences expressed from genes containing germ-line mutations. The sequences may be expressed as mRNA and amplified for example by reverse transcription-PCR, with incorporation of a label. The sequences may also be from viral RNA present in infected cells or tissue, or in extracts from infected cells or also tissue, or present in the virion particle itself. The test RNA sequences may also be unamplified endogenous mRNA or viral RNA.

7. Production of Test Duplexes

The test duplexes may also be produced by hybridization of complementary strands of experimental and normal control nucleic acid, especially RNA, which are derived from recombinant plasmids or recombinant DNA molecules in vectors other than plasmids, such as phagemids, bacteriophage, or artificial yeast or human chromosome vectors. The complementary nucleic acid strands may be produced by in vitro transcription of the recombinant inserts using bacteriophage promoters contained in the vectors themselves, or by in vitro transcription of sequences amplified from the recombinant vectors using primers containing appropriate promoter sequences, for example bacteriophage promoters, such that the amplified products have promoters incorporated at their 5' ends. The recombinant inserts may be unmodified sequences cloned directly from sources such as genomic DNA, mitochondrial DNA, or expressed as mRNA or other cellular or viral RNAs (using reverse transcription to copy the RNA sequences into DNA to allow them to be cloned). Alternatively, the recombinant inserts may be the products of random or targeted mutagenesis schemes which introduce one or more mutations into the cloned sequences, either before or after they are inserted into the vector.

8. Use of Microtiter Plates

A preferred embodiment of the present invention includes detecting mutations in samples wherein the in vitro transcription reactions are carried out in microtiter plates. The reaction components may be incubated for about 0.5–1 hour at 37° C., and terminated by the addition of an equal volume of hybridization solution containing a high concentration of formamide (for example, 80%). They may then be heated for about one minute at about 95° C.; the heating may be performed by placing the microtiter plate in a thermalcycler. Either prior or subsequent to heating the products of the in vitro transcription reaction, complementary experimental and normal transcripts may be mixed to make the duplex RNA substrates for RNase digestion.

The RNase digestion reactions may then be carried out in individual wells of microtiter plates, such as standard disposable U-bottom non-sterile polystyrene 96-well plates (sold by Dynatech Laboratories, Inc, 14340 Sullyfield Circle, Chantilly, Va., 22021; cat. no. 001-010-2205). Mixing of the duplex RNA substrates with the RNase solution may be accomplished by gently tapping and/or rotating the plates manually, or by specially designed mechanical vortexing devices. During incubation of the RNase digestion reactions, the wells of the microtiter plate may be covered with the adhesive film provided by the vendor with the plates, to prevent evaporation of the reactions. After incubation, the gel loading solution may be added and mixed with the RNase digestion reaction, and the contents of each well loaded on a native gel, typically a 2% agarose gel, and analyzed as in Example 1.

By performing the reactions in microtiter plates, the cost and labor associated with the assay is reduced, compared to carrying out the reactions in microfuge tubes. In addition, the feasibility of using automated devices, for example robotic arms, designed for high-throughput liquid handling, is increased. In contrast to the Non-Isotopic RNase Cleavage Assay described herein, the standard RNase cleavage-based mutation detection method requires organic extraction and alcohol precipitation of RNase cleavage products, and thus does not lend itself readily to being carried out in microtiter plates or to automation.

9. Detection Methods

Another preferred embodiment of the present invention encompasses the use of automated fluorescent photodetectors for analysis of RNase cleavage products, such as those used for automated DNA sequencing, to detect the size-fractionated RNase cleavage products generated. The photodetector and associated wavelength filters may be appropriate for detecting products which emit light of a given wavelength, for example in the orange-red range, when stained with ethidium bromide and excited with light in the ultraviolet range. If nucleic acid stains other than ethidium bromide are used, the specific detection properties of the photodetector, i.e., the wavelengths at which the products are excited and detected, may be varied for their specific detection. The photodetector may be placed at a position, for example at the end of an agarose gel distal to that of sample loading, which is appropriate to detect electrophoretically separated subfragments of the duplex RNA substrates. Use of an automated fluorescent photodetector will facilitate the acquisition and processing of data required to fully automate genetic screening based on the Non-Isotopic RNase Cleavage Assay described herein.

The present invention may also be employed to detect mutations as cleavage products which are denatured and analyzed as single strands. The present methods enable the detection of mismatches by analysis of single stranded nucleic acid probes, especially RNA probes, which may be labeled by radioisotopes or by other means, or unlabeled, and hybridized to DNA or RNA targets according to the NIRCA™ method (U.S. application Ser. No. 08/371,531) or according to the method of Maniatis et al., (U.S. Pat. No. 4,946,773, 1990).

In a preferred method, after hybridization, the duplex nucleic acid targets may be treated with RNase(s) or other potentially appropriate nucleases, for example, S1 Nuclease or Mung bean nuclease, using the digestion conditions of the present disclosure as set forth in Example 1. After nuclease treatment, the nuclease may be inactivated, by protease digestion, by denaturation with SDS or guanidinium, or by other means. The cleavage products may then be recovered, with alcohol precipitation, and the two strands denatured, by heating in a solution containing formamide. The cleavage products may be analyzed in a manner that maintains them as single strands by electrophoresis on a denaturing polyacrylamide gel. Cleavage products may be detected in a manner appropriate for the way in which they are labeled, by fluorescence under UV light or light of another wavelength, by autoradiography, by silver staining, or by secondary detection methods using binding and detection of streptavidin, as the case may be.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

B. EXAMPLES

Example 1

RNase Cleavage Assay for the Detection of Mutations.

In performing an RNase cleavage assay of base pair mismatches, the inventor currently prefers to use certain compositions and steps, which are set forth in the present example.

1. Both strands (sense and antisense) of the test and control target regions are transcribed into RNA. Preferably, transcription reactions contain mass amounts of unlabeled ribonucleotides sufficient to generate several micrograms of transcript at a concentration of about 100–500 $\mu$g/ml. Typical in vitro transcription reactions contain:

A. 2 $\mu$l PCR template with opposable promoters, for example, T7 and SP6 promoters;

B. 2 $\mu$l of a 5x buffer of buffer containing salts, spermidine, and buffering and reducing agents. The 5x transcription buffer contains:
  (a) 200 mM Tris-Cl pH 8;
  (b) 40 mM $MgCl_2$;
  (c) 10 mM spermidine; and
  (d) 250 mM NaCl as described in *Current Protocols in Molec. Biology* (1) 4.7.5.

C. 2 $\mu$l of a mixture containing all 4 ribonucleotide triphosphates, each at a concentration of 2.5 mM;

D. 4 $\mu$l distilled $H_2O$; and

E. 1 $\mu$l of 20 units/$\mu$l RNA polymerase, eg. T7 or SP6 RNA Polymerase.

The template for the in vitro transcription reaction generally contains amplified products from test or wildtype control target regions. Alternatively, the test and wildtype control target regions may both exist in a single sample amplified from a heterozygous source. The RNA polymerase used may be a mixture of polymerases, for example T7 and SP6.

The reactions are incubated and terminated according to standard procedures. Preferably, they are terminated by heating in an equal volume of buffer containing a high formamide and low salt concentration, for example, 80% formamide/25 mM sodium citrate at pH 6.8.

2. The sense and antisense products of the in vitro transcription reactions are mixed such that complementary transcripts derived from wildtype control and test target regions are able to hybridize and form double-stranded RNA molecules. The complementary sense and antisense transcripts derived from the wildtype control template are also mixed and hybridized. Typically, at least 2 $\mu$l of each transcription reaction is mixed with 2 $\mu$l of its complement, heated briefly (~3 minutes) at 80–100° C., and allowed to cool to ambient temperature over a period of several minutes. When the template for the transcription reaction included a mixture of control and test target templates, such that both test and wildtype complementary transcripts were produced simultaneously, in the in vitro transcripts reaction, this mixing step may not be required.

3. The hybridized wildtype control and test transcripts (RNA test duplexes), and also the hybridized complementary wildtype control transcripts (RNA control duplexes), are treated with ribonuclease(s) or other enzymes or agents such that cleavage of target duplexes containing base pair mismatches takes place to generate products which are altered in size compared to the control duplex treated in the same way. Preferably, the volume of solution (for example nuclease solution) added to the RNA duplexes should be sufficiently small that the final reaction products can be analyzed directly on a gel. For example, 16 $\mu$l of a solution containing a nuclease capable of cleaving base pair mismatches is typically added to 4 $\mu$l of an RNA duplex, mixed, and incubated at 37° C. for 20 to 60 minutes.

The solution added to the RNA/RNA or RNA/DNA duplex also may contain 32 mg/ml tryptone, 100 $\mu$g/ml ethidium bromide, and one or more of the following ribonucleases: RNase I, at about 100 to about 300 units/ml; RNase A, at 0.3 $\mu$g/ml; RNase T1, at about 64,000–160,000 units/ml (equivalent to about 100–250 $\mu$g/ml). With the addition of 4 μl the test duplex, the final concentration will become about 80 μg/ml ethidium bromide and about 25 mg/ml tryptone.

Alternatively, the solution added to the RNA/RNA or RNA/DNA duplex may contain 25 μg/ml ethidium bromide, 25 mg/ml tryptone, 85 mM NaCl, and one or more of the following ribonucleases: RNase I, at 500–1000 units/ml; RNase A, at 0.1–0.5 μg/ml; RNase T1, at 64,000–160,000 units/ml. If the ribonuclease used is RNase T1, the tryptone may be omitted from the solution.

4. The reaction products are analyzed in the double stranded state, to detect size differences in the test duplexes compared to the control duplex. Typically, a small amount (~⅙–⅒ volume) of a dense, loading solution is added to all samples, which are then loaded directly, without heating, onto a non-denaturing gel, typically 2% agarose in 1X TBE. 1X TBE is Tris-borate-EDTA electrophoresis buffer; 90 mM Tris/borate. 2mM EDTA containing 0.5 μg/ml ethidium bromide. The nucleic acid fragments in each sample are separated according to size by running the gel, i.e., by electrophoresis at 80 volts for 30 minutes in a buffer containing 1X TBE.

The fragments are visualized by staining with a dye that binds to double-stranded nucleic acid, such as ethidium bromide. The ethidium dye may be added to the sample, the gel, and/or the buffer, or the finished gel may be soaked in solution containing ethidium bromide. The dense loading solution may also contain ingredients such as tetramethylammonium chloride or ethidium bromide that cause the nucleic acid fragments to migrate as sharp bands, rather than diffuse bands, which would be difficult to analyze. The gels are illuminated with ultraviolet light to visualize the ethidium-stained nucleic acid fragments. When the RNase digestion buffer contains ethidium (as in the present invention), it is not necessary to add it to the gel or the electrophoresis buffer.

Test samples containing nucleic acid fragments which are not seen in the no-mismatch control reaction are scored as positive for containing base pair mismatches, which result from mutations in the test target region being screened. The test samples may be derived from nucleic acid targets amplified from chromosomal DNA (i.e., genomic DNA) from prokaryotic or eukaryotic sources, including plant, animal, bacterial, fungal, or protozoan genomes, or from mitochondrial DNA from plant or animal or fungal eukaryotic sources.

Example 2

Cleavage of Mismatches using Prior Art and Current Invention Compositions for RNase I Digestion Buffer This experiment describes the cleavage and detection of mutations using the inventive buffers disclosed in this patent as compared with buffers that have previously been reported. Double-stranded RNA targets were prepared by in vitro transcription of PCR products containing opposable T7 and SP6 promoters, according to the basic NIRCA™ method. Targets were 582 bp regions of the clotting Factor IX gene, amplified from genomic DNA from Hemophilia B patients having known mutations in exon 8.

Figure 1:
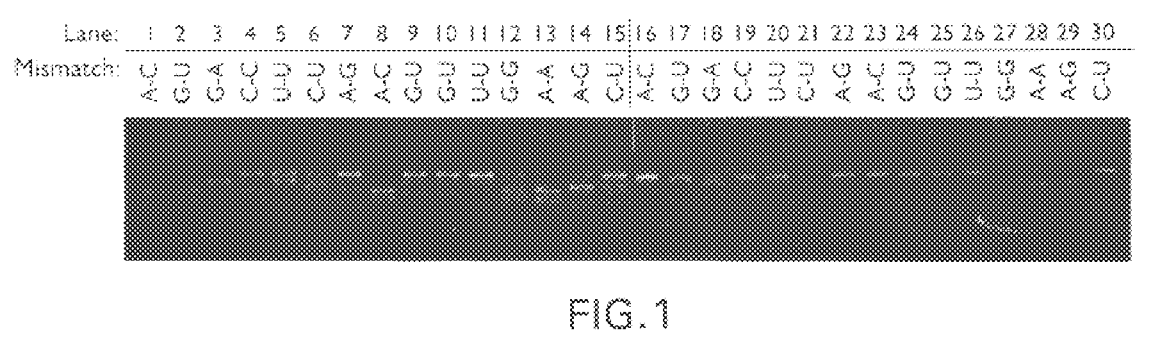

FIG. 1 shows the results of comparing the detection of mutations by buffers of the present invention and the prior art. The mismatches resulting from hybridization of patient sense strand and wildtype antisense strand transcripts are shown above the lanes. Samples in the left side of FIG. 1 (lanes 1–15) were treated with 2.6 units/reaction (0.165 units/μl) of RNase I in a buffer containing 32 grams/liter tryptone, 100 μg/ml ethidium bromide, and 50 μg/ml carbenicillin (to prevent bacterial growth); this is one of the preferred buffer compositions of the present invention. Duplicate samples in the right side of FIG. 1 (lanes 16–30) were treated with 53 units/reaction (3.3 units/μl) of RNase I in a buffer containing 10 mM Tris pH 7.5, 5 mM EDTA, and 200 mM sodium acetate; this is the buffer composition given in the prior art (Promega, Inc.). All samples were incubated for 45 minutes at 37° C., and analyzed on a 2% agarose gel according to the standard NIRCA™ procedure.

Many mismatches cleaved in lanes 1–15 employing the buffer of this invention were not cleaved or were less completely cleaved, as compared to the same samples in lanes 16–30 by the prior art buffer, despite the fact that 20-fold greater amount of RNase I was used to treat the samples in lanes 16–30.

Example 3

Cleavage of Mismatches using an RNase T1 Digestion Buffer

This example details the detection of mutations employing RNase T1 buffers of the present invention. Double-stranded RNA targets containing mismatches due to point mutations in exon 8 of the Factor IX gene were prepared as described in Example 2.

The results are illustrated in FIG. 2. Mismatches in each sample are shown above the lanes; the lanes labeled "wt" contain the wildtype (no-mismatch) control sample. Samples were treated with RNase T1 at a concentration of 250 μg/ml for 45 minutes at 37° C. and analyzed on 2% agarose gels according to the standard NIRCA™ protocol. The digestion buffer used for the samples shown on the left side of FIG. 2 (lanes 1–15) contained 32 grams/liter tryptone, 100 μg/ml ethidium bromide, and 50 μg/ml carbenicillin; this is one of the preferred buffer compositions of the present invention. The digestion buffer used for the duplicate samples shown on the right side of FIG. 2 (lanes 16–30) contained 10 mM Tris pH 7.5 and 300 mM sodium chloride; this is the composition of the standard buffer used for RNase A cleavage in the prior art (Winter et al., 1985), except that the EDTA was omitted. (Since RNase T1 has not previously been widely used for mismatch cleavage, there is no prior art for an RNase T1-mismatch digestion buffer.) Many mismatches cleaved in lanes 1–15 were not cleaved or were less completely cleaved, as compared to the same samples in lanes 16–30.

Example 4

Cleavage of Mismatches using a Digestion Buffer with Calcium

This example teaches the cleavage and detection of mutations employing calcium instead of tryptone as the basepair mismatch cleavage enhancing agent in the digestion buffer. Double-stranded RNA targets containing mismatches due to point mutations in exon 8 of the Factor IX gene were prepared as described in Example 2. Replicate panels of 6 targets were treated with RNase I (0.165 units/μl; 2.6 units/reaction) in one of five different digestion buffers and analyzed on a 2- agarose gel according to the standard NIRCA™ protocol.

Figure 3:
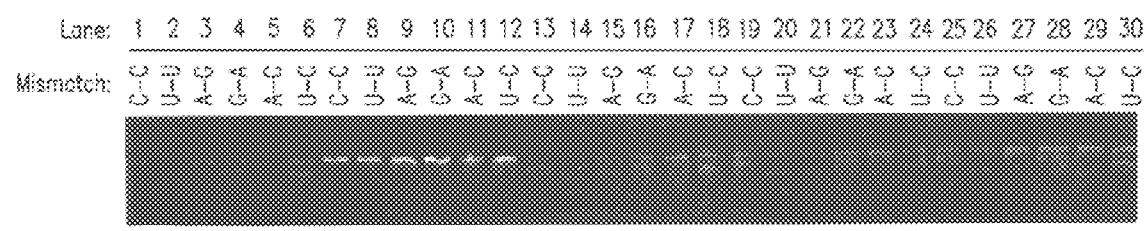
FIG. 3: Cleavage of mismatches using digestion buffer with calcium instead of tryptone.

The results are depicted in FIG. 3. Mismatches in each sample are shown above the lanes. Lanes 1–6 show the results of employing a preferred digestion buffer of this invention that contained 32 grams/liter tryptone and 100 μg/ml ethidium bromide. In this case, cleavage products were generated in all samples.

In lanes 7–12, the results are illustrated for a digestion buffer that contained 10 mM Tris pH 7.5, 40 mM sodium chloride, and 100 μg/ml ethidium bromide. Note that no cleavage products were generated.

In lanes 13–18, another preferred digestion buffer of this invention was employed. This buffer contained 10 mM Tris pH 7.5, 40 mM sodium chloride, 100 μg/ml ethidium bromide, and 1.5 mM calcium chloride (the same as that used in Lanes 7–12, except that calcium chloride was added). Cleavage products were again seen in all samples. Lanes 19–24 also employed a digestion buffer that was the same as in lanes 7–12, except that calcium chloride was added to 2.5 mM. Cleavage products were again seen in all samples. Lanes 25–30 also used a digestion buffer that was the same as in Lanes 7–12, except that calcium chloride was added to 4 mM. Cleavage products were also seen in all samples.

Example 5

Cleavage of Mismatches in the Presence of Acridine Orange

This example details the cleavage and detection of mismatches by digestion buffers containing acridine orange. Double-stranded RNA targets containing mismatches due to point mutations in exon 8 of the Factor IX gene were prepared as described in Example 2. Replicate panels of 6 targets were treated with RNase I (1 unit/μl; 16 units/reaction) in one of five different digestion buffers and analyzed on a 2% agarose gel according to the standard NIRCA™ protocol.

Figure 4:
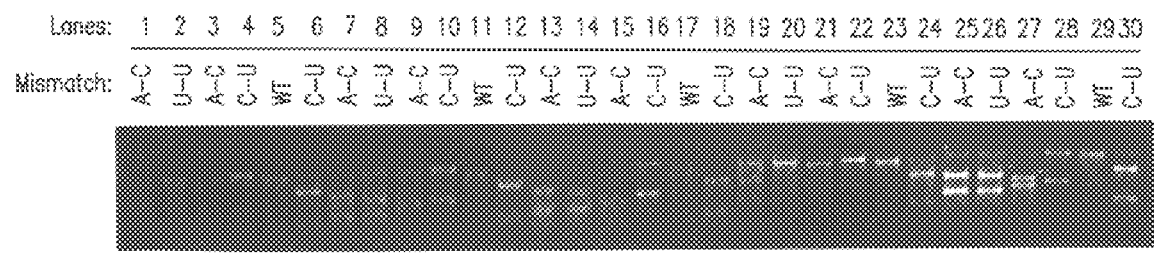
FIG. 4: Cleavage of mismatches in the presence of acridine orange.
Figure 5A:
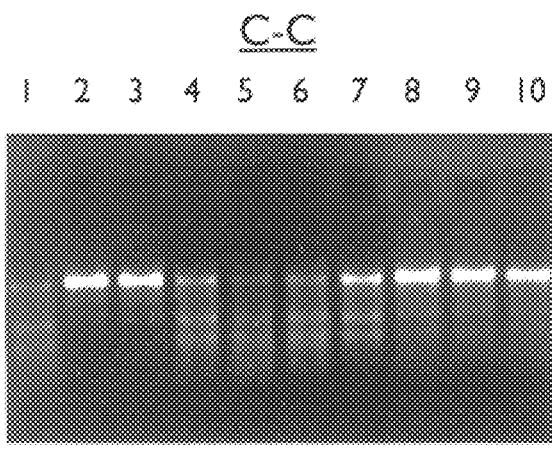
FIGS. 5A–5E: Effects of tryptone, calcium and the metal chelators EDTA and EGTA on mutation cleavage.
Figure 5B:
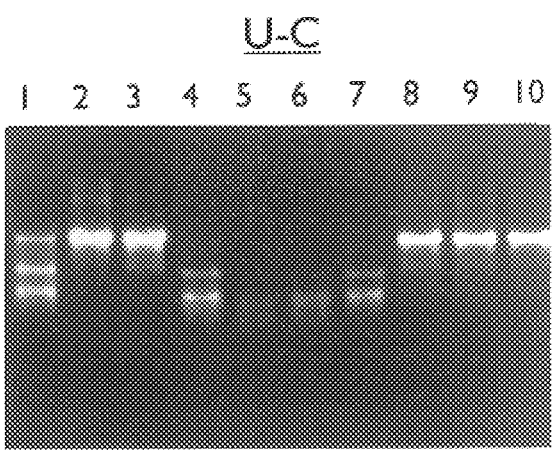
Figure 5C:
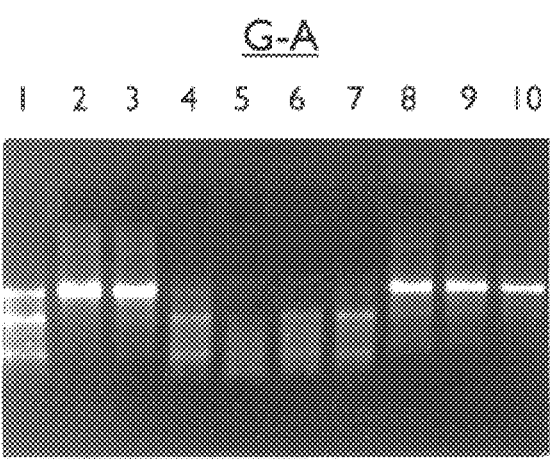
Figure 5D:
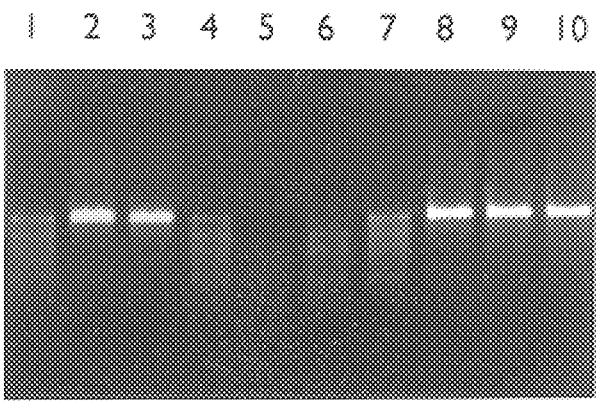
Figure 5E:
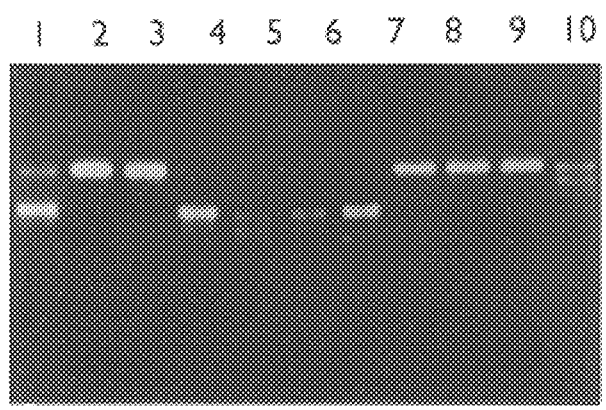

FIG. 4 depicts the results of this example. The mismatches in each sample are shown above the lanes; the lanes labeled "wt" contain the wildtype (no-mismatch) control sample. The basal digestion buffer used for all samples contained 32 grams/liter tryptone and 85 mM sodium chloride. In addition, intercalating agents (acridine orange or ethidium bromide) were added to some samples as follows: Lanes 1–6: 5 μg/ml acridine orange; Lanes 7–12: 10 μg/ml acridine orange; Lanes 13–18: 20 μg/ml acridine orange; Lanes 19–24: no intercalating agent; Lanes 25–30: 10 μg/ml ethidium bromide. Cleavage of most mismatches was improved in the presence of an intercalating agent. The cleavage products migrate as bands that are more diffused in the presence of acridine orange, compared to their migration in the presence of ethidium bromide.

Example 6

The Interrelationship of Tryptone and Calcium and the Metal Chelators EDTA and EGTA This example describes the interrelationship between tryptone and calcium in the practice of the present invention. For example, the beneficial effects of tryptone for mismatch cleavage can be duplicated by calcium and are abolished by EDTA and EGTA. Double-stranded RNA targets containing mismatches due to point mutations in exon 8 of the Factor IX gene were prepared as described in Example 2.

The results are illustrated in FIG. 5A, FIG. 5B, FIG. 5C, FIG. 5D, and FIG. 5E. Each target was treated with RNase I (0.165 units/μl) under 10 different RNase digestion buffer conditions, which correspond to the lane numbers in FIG. 5A, FIG. 5B, FIG. 5C, FIG. 5D, and FIG. 5E: in conditions 1, 8, 9, and 10, the digestion buffer contained 32 grams/liter tryptone and 100 μg/ml ethidium bromide ("tryptone buffer"); in conditions 2, 3, 4, 5, 6, and 7, the digestion buffer contained 10 mM Tris pH 7.5, 40 mM sodium chloride, and 100 μg/ml ethidium bromide ("defined buffer"). Some reactions contained calcium (added as calcium chloride) as follows: condition 3: 0.1 mM calcium; condition 4: 1 mM calcium; condition 5: 2.5 mM calcium; condition 6: 5 mM calcium; condition 7: 10 mM calcium. Some reactions contained a divalent cation chelating agent as follows: condition 8: 1 mM EDTA; condition 9: 3 mM EDTA; condition 10: 1 mM EGTA. The mismatch in each target is indicated above each figure.

The presence of cleavage products was detected when using the tryptone buffer (condition 1), and the cleavage products were absent when using the defined buffer without calcium (condition 2). Cleavage products were seen in the defined buffer when calcium is added to 1 mM (condition 4), but not when calcium was added to only 0.1 mM (condition 3). Addition of calcium to levels above 1 mM resulted in overdigestion of the target duplex (conditions 5, 6, and 7). When the tryptone buffer was used, addition of EDTA to 1 mM or 3 mM (conditions 8 and 9), or addition of EGTA to 1 mM (condition 10), prevented the mismatch from being cleaved.

Example 7

Cleavage of Mismatches in p53 Targets by RNase A, RNase I, and RNase T1

This example describes the cleavage of mismatches in p53 targets by digestion buffers of the present invention and RNase A, RNase I, or RNase T1. p53 is a tumor suppressor included in cancer. The ability to detect mutations in the p53 gene allows one's cancer-susceptibility to be determined. This example therefore demonstrates the utility of the present invention in a clinical environment. Double-stranded RNA targets were prepared by in vitro transcription of PCR products containing opposable T7 and SP6 promoters, according to the basic NIRCA™ method. Targets were 781 bp coding regions (exons 4–10) of the p53 tumor suppressor gene, amplified by RT-PCR from total RNA samples isolated from unselected breast tumors. The RNase digestion buffer for all samples contained 32 grams/liter tryptone and 100 μg/ml ethidium bromide.

Figure 6A:
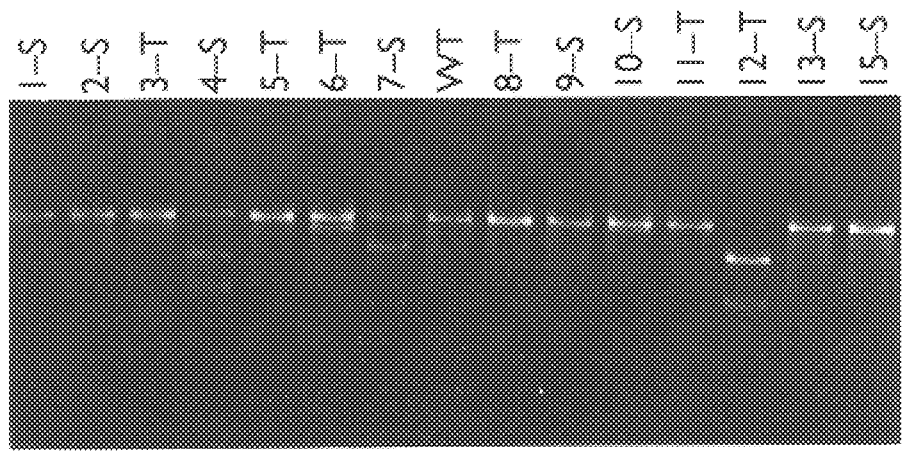
FIGS. 6A–6C: Cleavage of mismatches in p53 targets by RNase A, RNase I, and RNase T1.
Figure 6B:
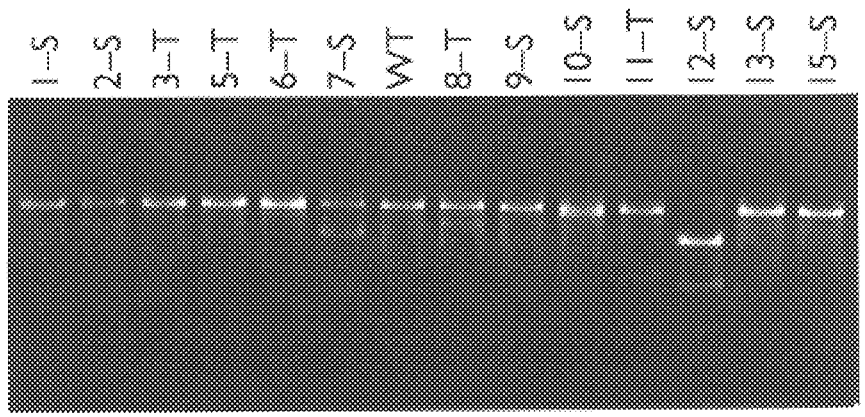
Figure 6C:
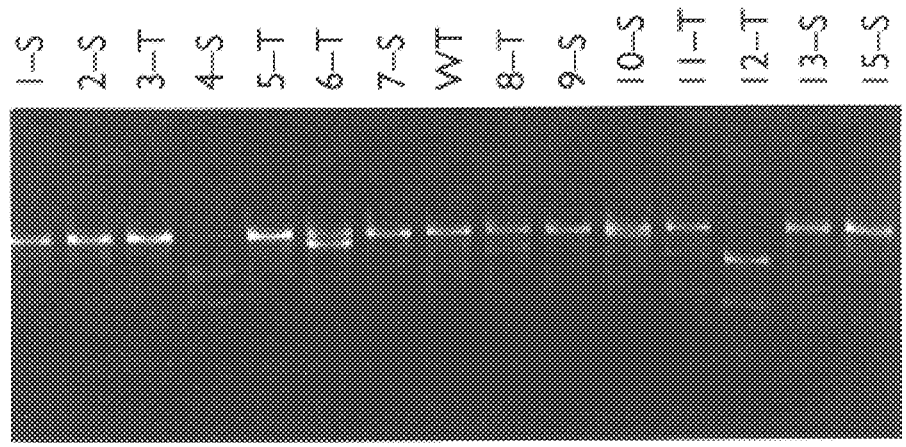

The results are shown in FIG. 6A, FIG. 6B and FIG. 6C. The RNases used to treat the samples were as follows: FIG. 6A: RNase I, 0.165 units/μl; FIG. 6B: RNase T1, 250 μg/ml; FIG. 6C: RNase A, 0.3 μg/ml. The sample numbers are shown above the lanes; samples designated "T" were prepared by hybridizing experimental Antisense strands with wildtype Sense-strand transcripts; samples designated "S" were prepared by hybridizing experimental sense strands with wildtype antisense strands. Lanes labeled "wt" contain the wildtype (no-mismatch) control sample.

Some samples showed cleavage products with more than one RNase. The cleavage products were due to putative p53 point mutations in the experimental samples; the nature of the mutations is presently being determined by direct sequencing of PCR products. Some samples did not show cleavage products with any of the three RNases; these are putatively negative for p53 point mutations.

Example 8

Cleavage of Mismatches in Large Panel of Homozygous and Heterozygous Samples with Factor IX Mutations This example details the cleavage and detection of mismatches with digestion buffers of the present invention in large panel homozygous and heterozygous samples with Factor IX mutations. Double-stranded RNA targets containing mismatches due to point mutations in exon 8 of the Factor IX gene were prepared from genomic DNA isolated from Hemophilia B patients and heterozygous carriers, as described in Example 2.

Figures 7A, 7B:
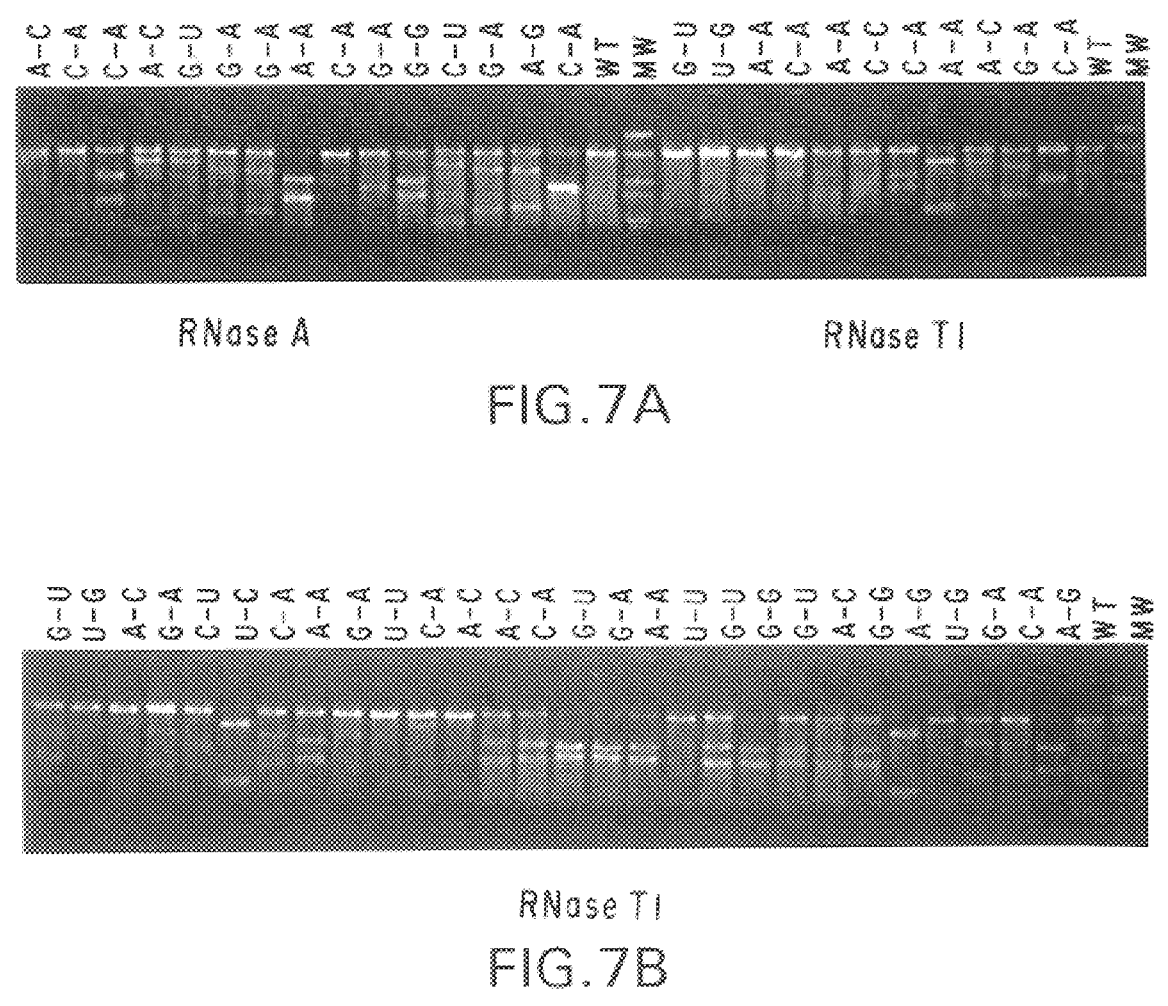

The results are illustrated in FIG. 7A and FIG. 7B. The mismatches in each sample are shown above the lanes. Samples from heterozygous carriers are designated with a suffix "H". Lanes designated "wt" contain wildtype (no-mismatch) control sample. The RNase digestion buffer used for all samples contained 32 grams/liter tryptone and 100 μg/ml ethidium bromide. Lanes marked "mw" contained molecular weight markers (Sau 3A restriction fragments of plasmid pUC19); the sizes of the two largest mw fragments were 955 bp and 585 bp. The RNase used to treat each group of samples is indicated below the figure.

Specific cleavage products were generated in most but not all samples, by at least one (and usually more than one) of the three RNases. Samples that were negative with all three RNases (e.g., sample #15) were positive with at least one RNase when the reciprocal mismatch was tested (data not shown).

Example 9

Fractionation of the Protein Mixture to Identify the Component(s) Active in Enhancing RNase Cleavage of Mismatches This example describes how one might identify the various active components that result in enhancing the specific cleavage of base pair mismatches.

In order to identify the active component(s) in a protein mixture, such as tryptone, that are shown to be effective in improving mismatch detection in the RNase assay, it is contemplated that one may initially use ion exchange HPLC (high-performance liquid chromatography). Both cation and anion exchange resins may be used. Individual column fractions may then be assayed for their ability to replace tryptone in mismatch cleavage assays. Those fractions with cleavage enhancing activity may be scanned spectroscopically, in both visible and ultraviolet wavelengths, in order to identify relevant absorbance peaks. If fractions with mismatch cleavage enhancing activity do not correlate with any specific peaks, the fractions may be analyzed by flame spectroscopy for the presence of metals or other inorganic ions. Once the active substance has been identified, if it is not a metal ion, its identity may be determined by infrared spectroscopy. The abundance and low cost of the starting material, tryptone, will facilitate the isolation and identification of the active component.

As an alternative to the above scheme for identifying the active component, one may select components from the list of ingredients found in tryptone (see attached detailed biochemical analysis provided by Difco laboratories, the company which manufactures tryptone), and test individual components, such as vitamins, co-factors, and ions, for mismatch cleavage enhancing activity.

* * *

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Applicant hereby incorporates by reference the disclosure of U.S. patent application Ser. No. 08/371,531, filed Jan. 9, 1995, "Methods and Compositions for Detecting Base Pair Mismatches in Double-Stranded RNA" by Marianna Goldrick.

The following references, to the extent that they provide exemplary procedural or other details supplementary to those set forth herein, are specifically incorporated herein by reference.

Maniatis et al., U.S. Pat. No. 4,946,773.(Aug. 7, 1990).
Cannistraro and Kennell (1991) *Journal of Bacteriology* 173:4653–4659.
Cheng and Haas (1992) *PCR Methods and Applications* 1:199–201.
Cotton (1989) *Biochem J.* 263:1–10.
Ekenberg and Hudson (1994) *Promega Notes* 46:14–16.
Favre et al. (1993) *Journal of Bacteriology* 175:3710–3722.
Gabryszuk et al. (1995) *Gene* 161:1995.
Gesteland (1966) *Journal of Molecular Biology* 16:67–84.
Grompe (1993) *Nature Genetics* 5:111–117.
Hime et al. (1995) *Gene* 158:203–207.
Jermann et al. (1995) *Nature* 374:57–59.
Marquardt et al. (1991) *J. Virological Methods* 33:267–282.
Meador and Kennell, (1989) *Eur. J. Biochem.* 187:549–553.
McDowall et al. *Journal of Biological Chemistry* 269:10790–10796.
Myers et al. (1985) *Science* 230:1242–1246.
Promega Technical Manual (1992). RNase One, Standard Applications. Promega Corporation, 2800 Wood Hollow Road, Madison, Wis. 53711–5399.
Raines et al. U.S. Pat. No. 5,389,537, issued Feb.14, 1995.
Roberts (1995) *Cell* 82:9–12.
Sarkar et al. (1992) *Nucleic Acids Res.* 20:871–878.
Srivastava et al. (1992) *Journal of Bacteriology* 174:56–62.
Theophilus et al. (1989) *Nucleic Acids Research* 17:7707–7722.
Worthington Enzymes and Related Biochemicals Manual, 1993. Edit. Von Worthington, Worthington Biochemical Corp. Freehold, N.J. 07728. Phone: (800) 445-9603. Relevant section, pg 359.
Zhu et al. (1990). *Journal of Bacteriology* 172:3146–3151.

What is claimed is:

1. A method of cleaving double-stranded nucleic acid molecules containing base pair mismatches comprising:
   (a) obtaining a test nucleic acid duplex;
   (b) placing said test nucleic acid duplex in a reaction mixture that cleaves double-stranded nucleic acid molecules containing base pair mismatches under conditions effective to allow the formation of cleavage products, said reaction mixture comprising:
      (i) an RNase enzyme;
      (ii) a nucleic acid intercalating agent; and
      (iii) an RNase mismatch cleavage activity enhancing agent comprising a protein mixture, a divalent cation, or both; and
   (c) separating said cleavage products under conditions that allow the cleavage products to remain double-stranded.

2. The method of claim 1, wherein the double stranded nucleic acid is an RNA duplex.

3. The method of claim 1, wherein the RNase mismatch cleavage activity enhancing agent comprises a digested protein mixture.

4. The method of claim 1, wherein the RNase mismatch cleavage activity enhancing agent comprises a divalent cation.

5. The method of claim 4, wherein the divalent cation is $Ca^{++}$.

6. The method of claim 1, wherein the RNase enzyme is RNase I.

7. A method for detecting a base pair mismatch in a nucleic acid molecule; comprising the steps of:
  (a) obtaining a single stranded RNA test sample to be analyzed;
  (b) contacting said RNA test sample with a single stranded nucleic acid probe thereby forming a test duplex;
  (c) treating said test duplex with a ribonuclease composition that cleaves double-stranded RNA molecules containing base pair mismatches under conditions effective to allow the formation of cleavage products, said ribonuclease composition comprising:
    (i) an RNase enzyme;
    (ii) a nucleic acid intercalating agent; and
    (iii) an RNase mismatch cleavage activity enhancing agent comprising a protein mixture, a divalent cation, or both; and
  (d) separating said cleavage products under conditions that allow the cleavage products to remain double-stranded.

8. The method of claim 7, wherein the single stranded nucleic acid probe is RNA.

9. The method of claim 7, wherein the RNase mismatch cleavage activity enhancing agent comprises a digested protein mixture.

10. The method of claim 7, wherein the RNase mismatch cleavage activity enhancing agent comprises a divalent cation.

11. The method of claim 7, wherein said RNA test sample is obtained from a biological sample from a patient suspected of having a disease associated with a genetic mutation.

12. A method for identifying a mutation in a gene; comprising the steps of:
  (a) obtaining a single stranded RNA test sample from said gene and a single stranded RNA non-mutant control sample having the wild type sequence of said gene;
  (b) contacting said test RNA sample and said non-mutant control RNA sample with a single stranded RNA probe, thereby forming a test RNA duplex and a control RNA duplex;
  (c) treating said test RNA duplex and said control RNA duplex with a ribonuclease composition that cleaves double-stranded RNA molecules containing base pair mismatches, under conditions effective to allow the formation of cleavage products, said ribonuclease composition comprising:
    (i) an RNase enzyme;
    (ii) a nucleic acid intercalating agent; and
    (iii) an RNase mismatch cleavage activity enhancing agent comprising a digested protein mixture, a divalent cation, or both;
  (d) separating said cleavage products under conditions that allow the cleavage products to remain double-stranded; and
  (e) comparing the separated cleavage products from said test RNA duplex and said control RNA duplex, wherein a difference in the size of the cleavage products is indicative of the presence of a mutation in said gene.

13. The method of claim 12, wherein the RNase mismatch cleavage activity enhancing agent comprises a digested protein mixture.

14. The method of claim 12, wherein the RNase mismatch cleavage activity enhancing agent comprises a divalent cation.

15. The method of claim 12, wherein said single stranded RNA probe has a sequence of said wild type gene and forms a duplex with said control sample that does not contain a mismatch.

16. The method of claim 12, wherein said single stranded RNA probe has a sequence of said mutant gene and forms a duplex with said control sample that contains a mismatch.

17. The method of claim 12, wherein said single stranded RNA test sample is obtained from a patient suspected of having a disease associated with a genetic mutation.

18. A kit for use in conducting an RNase mismatch cleavage assay, the kit comprising, in a suitably aliquoted form, a means of generating RNA and an RNA digestion buffer comprising a protein mixture, a divalent cation, or both.

19. The kit of claim 18, wherein the RNA digestion buffer comprises a digested protein mixture.

20. The kit of claim 18, wherein the RNA digestion buffer comprises a divalent cation.

21. The kit of claim 18, wherein said means of generating RNA comprises a first and second PCR primer, each primer including a promoter sequence and a gene sequence from spatially separated regions of the same gene, and a RNA polymerase interactive with the promoter sequences of the primers.

22. The kit of claim 21, wherein said means of generating RNA further comprises a template gene sequence having the wild type sequence of said gene and a template gene sequence having the mutant sequence of said gene.

23. A method of screening for an RNase mismatch cleavage activity enhancing agent comprising:
  (a) obtaining a digested protein mixture;
  (b) fractionating the digested protein mixture into two or more fractions; and
  (c) testing a fraction of the digested protein mixture for RNase mismatch cleavage activity enhancing characteristics.

24. The method of claim 23, wherein the step of testing the fraction comprises:
  (a) preparing a test RNA digestion buffer comprising the fraction and an RNase enzyme;
  (b) preparing a control RNA digestion buffer substantially identical to the test RNA digestion buffer and comprising the same RNase enzyme, but not having the fraction;
  (c) performing parallel tests with both the test RNA digestion buffer and the control RNA digestion buffer to determine the relative activities of the RNase enzyme in the test and control buffers.

25. A method of cleaving double-stranded nucleic acid molecules containing base pair mismatches comprising:
  (a) obtaining a test nucleic acid duplex;
  (b) placing said test nucleic acid duplex in a reaction mixture that cleaves double-stranded nucleic acid molecules containing base pair mismatches under conditions effective to allow the formation of cleavage products, said reaction mixture comprising:

(i) a nuclease; and (ii) a nucleic acid intercalating agent; and (c) separating said cleavage products under conditions that allow the cleavage products to remain double-stranded.

26. The method of claim 25, wherein the double stranded nucleic acid is an RNA duplex.

27. A method of cleaving double-stranded nucleic acid molecules containing base pair mismatches comprising:

(a) obtaining a test nucleic acid duplex;

(b) placing said test nucleic acid duplex in a reaction mixture that cleaves double-stranded nucleic acid molecules containing base pair mismatches under conditions effective to allow the formation of cleavage products said reaction mixture comprising (i) an RNase enzyme; and (ii) an RNase mismatch cleavage activity enhancing agent comprising a divalent cation; and (c) separating said cleavage products.

28. The method of claim 27, wherein said double-stranded nucleic acid is an RNA duplex.

29. The method of claim 27, wherein said divalent cation is $Ca^{2+}$.

30. The method of claim 27, wherein the divalent cation is free $Ca^{2+}$ present in a concentration of 0.01 mM to 100 mM.

31. The method of claim 27, wherein the RNase enzyme is RNase I or RNase T1.

32. The reaction mixture of claim 27, wherein the RNase enzyme is present in a concentration of 0.01 μg/ml–500 μg/ml.

33. The method of claim 27, further comprising a nucleic acid intercalating agent.

34. The method of claim 33, wherein the intercalating agent is present in a concentration of 1–1000 μg/ml.

35. The method of claim 27, wherein the reaction mixture further comprises NaCl.

36. The method of claim 35, wherein the NaCl is present at a concentration of 5–300 mM.

37. The method of claim 27, wherein said RNase mismatch cleavage activity enhancing agent further comprises a protein mixture.

38. A method of cleaving double-stranded nucleic acid molecules containing base pair mismatches comprising:

(a) obtaining a test nucleic acid duplex;

(b) placing said test nucleic acid duplex in a reaction mixture that cleaves double-stranded nucleic acid molecules containing base pair mismatches under conditions effective to allow the formation of cleavage products, said reaction mixture comprising (i) an RNase enzyme; and (ii) an RNase mismatch cleavage activity enhancing agent comprising a digested protein mixture; and (c) separating said cleavage products.

39. The method of claim 38, wherein said protein mixture comprises tryptone, peptone, casamino acids, N–Z amine, yeast extract, an acid or enzymatic hydrolysate of casein, an acid or enzymatic hydrolysate of soy bean, an acid or enzymatic hydrolysate of meat protein, an acid or enzymatic hydrolysate of mixed protein, or brain-heart infusion.

40. The method of claim 38, wherein said protein mixture is present in a concentration of between about 0.2 and about 100 mg/ml.

41. The method of claim 36, wherein the RNase mismatch cleavage activity enhancing agent further comprises a divalent cation.

42. The method of claim 41, wherein the divalent cation is $Ca^{2+}$.

43. The method of claim 42, wherein the $Ca^{2+}$ is present in a concentration of 0.1 mM to 100 mM.

44. The method of claim 38, wherein the RNase enzyme is RNase I or RNase T1.

45. The method of claim 38, wherein the reaction mixture further comprises an intercalating agent.

46. A method of cleaving double-stranded nucleic acid molecules containing base pair mismatches comprising:

(a) obtaining a test nucleic acid duplex;

(b) placing said test nucleic acid duplex in a reaction mixture that cleaves double-stranded nucleic acid molecule containing base pair mismatches under conditions effective to allow the formation of cleavage products, said reaction mixture comprising (i) an RNase enzyme; and (ii) a nucleic acid intercalating agent that enhances RNase mismatch cleavage activity; and (c) separating said cleavage products.

47. The method of claim 46, wherein said reaction mixture further comprises an PNase mismatch cleavage activity enhancing agent.

48. The method of claim 47, wherein said RNase mismatch cleavage activity enhancing agent comprises a protein mixture.

49. The method of claim 47, wherein said RNase mismatch cleavage activity enhancing agent comprises divalent cations.

50. The method of claim 46, wherein said intercalating agent is ethidium bromide.

51. The method of claim 50, wherein said ethidium bromide is present is a concentration of 1–1000 μg/ml.

* * * * *

UNITED STATES PATENT AND TRADEMARK OFFICE
CERTIFICATE OF CORRECTION

PATENT NO. : 5,891,629

DATED : April 6, 1999

INVENTOR(S) : Marianna M. Goldrick

It is certified that error appears in the above-identified patent and that said Letters Patent is hereby corrected as shown below:

In claim 22, column 34, line 38, delete "a" and insert --an-- therefor.
In claim 41, column 36, line 14, delete "36" and insert --38-- therefor.
In claim 46, column 36, line 30, delete "molecule" and insert --molecules-- therefor.
In claim 47, column 36, line 38, delete "PNase" and insert --RNase-- therefor.

Signed and Sealed this

Twenty-eighth Day of September, 1999

Attest:

Q. TODD DICKINSON

Attesting Officer     Acting Commissioner of Patents and Trademarks

UNITED STATES PATENT AND TRADEMARK OFFICE
CERTIFICATE OF CORRECTION

PATENT NO. : 5,891,629
DATED : April 6, 1999
INVENTOR(S) : Marianna M. Goldrick

It is certified that error appears in the above-indentified patent and that said Letters Patent is hereby corrected as shown below:

On the title page item:

[57] Abstract, in line 7, delete the phrase "T2" and insert --T1-- therefor.

col. 8, line 55, delete the phrase "Ti" and insert --T1-- therefor.

Signed and Sealed this

Ninth Day of November, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO.   : 5,891,629
DATED        : April 6, 1999
INVENTOR(S)  : Marianna M. Goldrick It is certified that error appears in the above-identified patent and that said Letters Patent is hereby corrected as shown below:

Column 1,
Lines 5-6, please delete: "The government may own rights in the present invention pursuant to U.S. grant number CA57045" and insert therefor the following:

-- This invention was made with government suport under R44CA57045 awarded by the National Cancer Institute. The government has certain rights in the invention. --

Signed and Sealed this

Thirtieth Day of July, 2002

Attest:

JAMES E. ROGAN
Attesting Officer    Director of the United States Patent and Trademark Office